(12) United States Patent
Ume et al.

(10) Patent No.: US 10,578,586 B2
(45) Date of Patent: Mar. 3, 2020

(54) WELD ANALYSIS USING LAMB WAVES AND A NEURAL NETWORK

(71) Applicant: Georgia Tech Research Corporation, Atlanta, GA (US)

(72) Inventors: Ifeanyi Charles Ume, Atlanta, GA (US); Lei Yang, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 78 days.

(21) Appl. No.: 15/573,370

(22) PCT Filed: May 11, 2016

(86) PCT No.: PCT/US2016/031939
§ 371 (c)(1),
(2) Date: Nov. 10, 2017

(87) PCT Pub. No.: WO2016/183250
PCT Pub. Date: Nov. 17, 2016

(65) Prior Publication Data
US 2018/0136169 A1    May 17, 2018

Related U.S. Application Data

(60) Provisional application No. 62/159,686, filed on May 11, 2015.

(51) Int. Cl.
| *G01N 29/04* | (2006.01) |
| *G01N 29/34* | (2006.01) |
| *B23K 31/12* | (2006.01) |
| *B23K 31/00* | (2006.01) |

(52) U.S. Cl.
CPC ............ *G01N 29/04* (2013.01); *B23K 31/006* (2013.01); *B23K 31/125* (2013.01); *G01N 29/34* (2013.01); *G01N 2291/2675* (2013.01)

(58) Field of Classification Search
CPC ................ B23K 31/006; B23K 31/125; G01N 2291/2675; G01N 29/04; G01N 29/34
USPC .............. 702/35, 54, 56, 66, 67, 73, 74, 75; 73/599, 600, 622, 627
See application file for complete search history.

(56) References Cited

U.S. PATENT DOCUMENTS

| 4,924,063 A | 5/1990 | Buchel et al. |
| 5,439,157 A | 8/1995 | Geier et al. |
| 7,132,617 B2 | 11/2006 | Lee et al. |
| 7,565,252 B2 * | 7/2009 | Kim ..................... G01N 29/075 702/35 |
| 8,146,429 B2 * | 4/2012 | Ume ..................... G01N 29/11 73/599 |
| 8,256,296 B2 * | 9/2012 | Ume ..................... G01N 29/11 73/600 |
| 8,297,122 B2 * | 10/2012 | Ume ..................... G01N 29/07 73/600 |

OTHER PUBLICATIONS

Search Report and Opinion from PCT Application No. PCT/US16/31939 dated Aug. 16, 2016 (21 pages).

Yang, et al., "Inspection of Simulated Weld Penetration Depth Using Laser-Waves and Wavelet Signal Processing," 41st Annual Review of Progress in Quanittative Nondestructive Evaluation, Mar. 31, 2015, pp. 1386-1391, URL:http://scitation.aip.org/content/aip/proceeding/aipcp/1650>.

* cited by examiner

*Primary Examiner* — John H Le
(74) *Attorney, Agent, or Firm* — Troutman Sanders LLP; Ryan A. Schneider

(57) ABSTRACT

A CWT-based method to calculate transmission coefficients of different Lamb waves using individual LEU signals. A neural network was trained to accurately predict WPDs based on the transmission coefficients of selected Lamb waves and the LEU signal energy. The method is capable of inspecting WPDs quickly along welds in thin structures.

18 Claims, 32 Drawing Sheets

WPD along weld 1

WPD along weld 2

WPD along weld 3

WPD along weld 4

WPD along weld 5

WPD along weld 6

Weld 5

Weld 6

Weld 5

Weld 5

WELD ANALYSIS USING LAMB WAVES AND A NEURAL NETWORK

CROSS-REFERENCE TO RELATED APPLICATIONS

This application claims the benefit of U.S. Provisional Patent Application No. 62/159,686, filed 11 May 2015, which is hereby incorporated herein by reference in its entirety.

BACKGROUND OF THE INVENTION

1. Field of the Invention

The present invention relates to systems and methods of weld analysis using elastic waves. More particularly, the present invention relates to systems and methods of high speed measurement of weld penetration depths in thin structures using transmission coefficients of laser-generated Lamb waves and a neural network.

2. Description of Related Art

Butt joint welding is an essential process of joining parts in many industries. A cross section of a conventional butt weld depicts a variety of weld dimensions including weld penetration depth (WPD), reinforcement height (RH) and bead width (BW). Among them, WPD is an important geometric parameter that indicates weld quality and is used as a key quality control quantity.

WPD is a key measurement of weld quality because it directly affects the strength of welded parts. Traditionally, cut-check, i.e., physically cutting the sample across the weld, has been widely used to monitor weld quality. This procedure, however, is time-consuming, destructive, and wasteful. In addition, automated inspection using cutcheck is not possible.

For at least the preceding reasons, it is desirable to perform non-destructive testing ("NDT") on a variety of materials to detect and locate, for example and not limitation, material defects, manufacturing defects, and weld quality. As a result, considerable resources have been invested to develop NDT methods such as, among other things, ultrasonic inspection, radiography, thermography, and eddy current inspection.

Ultrasonic inspection techniques have gained greater acceptance for a variety of purposes in recent years. It is one of the major techniques used, for example, for inspection of welds in structures. Conventionally, contact piezoelectric transducers (PZTs) have been used to generate and receive ultrasounds during offline, as opposed to real-time, sample inspection. Due to the need for liquid couplants between the PZTs and the sample, however, this method is not suitable for automated real-time inspection during manufacture.

Non-contact ultrasonic sensing, on the other hand, has the potential to detect defects and discontinuities in real time. Among different conventional non-destructive weld inspection techniques, the laser electromagnetic acoustic transducer (EMAT) ultrasonic (LEU) technique attracts interests from industry because of its non-contact operation that enables it to be employed in real-time inspections. Nanosecond pulse width lasers such as, for example, Q-switched Nd:YAG lasers can be used to generate ultrasound.

In use, a high energy, very short duration pulse from the laser induces a rapid increase in the local temperature of the sample. The heated region expands thermoelastically and then slowly contracts when the laser pulse is momentarily shut off. The rapid expansion and slower contraction creates ultrasounds which propagate through the sample. In addition to the thermoelastic effect, ablation can occur if the energy of the laser pulse is increased to the point that some portion of the surface evaporates. The ultrasounds generated in the ablation regime are much stronger than those generated in the thermoelastic regime, though the latter is generally preferred for true NDT.

Conventionally, a laser or a laser phased array system has been used to generate ultrasounds (i.e., bulk waves) to measure various characteristics in thick structures (e.g., weld penetration). A Time of flight diffraction (ToFD) technique can be used to evaluate, for example, material defects or weld characteristics. By measuring the arrival time of an ultrasonic signal, for example, various characteristics of weld such a penetration depth can be measured.

When the thickness of the sample approaches the wavelength of the ultrasonic wave, however, this method no longer provides accurate data. For thin materials, ultrasonic waves give way to Lamb waves, which exhibit very different characteristics compared to the bulk waves that travel in thick structures. As used herein, "thin" is defined as that thickness of a sample where such Lamb waves are generated.

Lamb waves travel through the cross section of the structure, are dispersive, and their traveling speeds are dependent on their frequencies. Lamb waves are widely used in structural integrity inspection and defect detection in thin structures because of their potentials to inspect large area and their sensitivity to a variety of damage types.

The use of lasers to generate Lamb waves is beneficial due to its noncontact nature. Laser generated ultrasound is broadband in nature, however, and this, combined with the dispersive nature of Lamb waves, makes signal processing complicated. To simplify signal processing in thin structures, therefore, narrowband Lamb waves are desirable.

Extensive studies have been conducted to use the LEU technique to measure WPDs in thick structures. Laser-generated ultrasounds in thick structures are bulk waves and surface waves, which propagate in all directions, as shown in FIG. 1(a). WPDs can be determined by tracing a specific wave path from the laser source to the EMAT receiver, which closely interacts with the weld bead. The time of flight (ToF) of waves following the selected wave path was shown to have a close-form mathematical relationship with the penetration depth of the weld bead.

As structural thickness decreases, laser-generated ultrasounds become Lamb waves. Lamb waves propagate in directions parallel to structure surfaces, as shown in FIG. 1(b). There is no internal wave path to trace, and therefore the method used in thick structures is not applicable to the study of thin structures.

Therefore, new indicators that are sensitive to WPDs need to be found in received signals in order to apply the LEU technique in thin structures. One challenge is that the LEU signals acquired in thin structures contain multi-modal and broadband Lamb waves, which are very complicated.

The present invention overcomes the many disadvantages present in the conventional WPD technologies by utilizing an effective and efficient method to apply the LEU technique to measure WPDs in thin structures.

BRIEF SUMMARY OF THE INVENTION

In an exemplary embodiment of the present invention, a fast, efficient, non-contact and non-destructive technique for measuring weld penetration depths in thin structures is presented.

An apparatus for non-destructively analyzing a weld in a sample can comprise an elastic wave source for generating elastic waves in a welded specimen on one side of a weld seam, an elastic wave sensor disposed on an opposite side of the weld seam from the elastic wave source for detecting elastic waves that are propagated from the one side of the weld seam to the opposite side, an assembly for moving the elastic wave source and the elastic wave sensor along a portion of the length of the weld seam, and a processor assembly for processing a transmission coefficient of the elastic wave sensed at a sensed location along the length of the weld seam to compute a weld penetration depth at the sensed location.

The plurality of weld penetration depths can be computed at a plurality of sensed locations within the portion of the length of the weld seam traversed by the elastic wave source and the elastic wave sensor.

The processor assembly can convert the elastic wave sensed at the sensed location into its time-frequency domain. The processor assembly can convert the elastic wave sensed at the sensed location into its time-frequency domain using complex-valued Morlet wavelets and continuous wavelet transform (CWT).

The processor assembly can calculate a transmission coefficient of the elastic wave at a sensed location based on the CWT of a signal received by the elastic wave sensor.

The processor assembly can comprise a neural network developed from the transmission coefficients and the signal energy to compute weld penetration depths at the sensed locations.

An apparatus for non-destructively analyzing a weld in a sample can comprise an elastic wave source for generating elastic waves in a welded specimen on one side of a weld seam, and an elastic wave sensor disposed on an opposite side of the weld seam from the elastic wave source for detecting elastic waves that are propagated from the one side of the weld seam to the opposite side.

The elastic wave source can comprise an industrial Nd:YAG (neodymium-doped yttrium aluminum garnet) pulsed laser that excites broadband Lamb waves from one side of weld seam to the other. The elastic wave sensor can comprise, for example, a receiving sensor, an electromagnetic acoustic transducer (EMAT), or a laser interferometer, to detect signals from the other side of the weld seam.

In an exemplary embodiment, the laser is delivered through a convex lens focused to a point source on the sample.

During an inspection process, the laser-receiving sensor pair moves along the weld seam to inspect weld penetration depths at different locations. The single signal acquired at each location is then converted to its time-frequency domain using, for example, complex-valued Morlet wavelets and continuous wavelet transform (CWT).

The present invention then calculates the transmission coefficients of different laser-generated Lamb waves based on the CWT of the individual signal. The calculated transmission coefficients and the signal energy then are used to develop a neural network to accurately predict the weld penetration depth at the location where the signal is acquired. The calculation of the transmission coefficients and the neural network are computationally efficient, which makes the present invention suitable for on-line inspections.

In another exemplary embodiment, the present invention is a fast, efficient, non-contact and non-destructive method for measuring weld penetration depths in thin structures comprising exciting broadband Lamb waves in a sample from one side of a weld seam by an Nd:YAG pulsed laser, detecting the Lamb waves with a receiver on the other side of the weld seam, moving the laser and receiver along a portion of the length of the weld seam (or moving the sample relative to a substantially fixed laser/receiver assembly), converting the Lamb wave signals to its time-frequency domain, calculating transmission coefficients of different laser-generated Lamb waves based on the time-frequency domain of the signal, and developing a neural network with the transmission coefficients and the signal energy, wherein the neural network predicts the measuring weld penetration depths along the length of the weld seam.

The method can further comprise delivering the laser through a convex lens to a focused point source the sample.

In another exemplary embodiment, the present invention is a method for non-destructively analyzing a weld in a sample comprising activating a pulsed, concentrated energy source to create Lamb waves in the sample, receiving the Lamb waves with a receiver, storing the signal generated by the receiver on a computer readable medium, providing relative movement between the sample, the energy source and the receiver, repeating the steps of activating, receiving, storing and providing relative movement until a predetermined analyzing length has been reached and a plurality of signals generated by the receiver have been stored on the computer readable medium, and creating a model correlating the plurality of signals generated by the receiver with empirical data for the sample.

The method can further comprise retrieving the signals stored on the computer readable medium, converting each signal to its time-frequency domain, calculating transmission coefficients of different laser-generated Lamb waves based on the time-frequency domain of the signal, and developing a neural network with the transmission coefficients and the signal energy, wherein the neural network predicts the measuring weld penetration depths along the length of the weld.

In another exemplary embodiment, the present invention is a system for non-destructively analyzing a weld seam in a sample comprising a concentrated energy source for creating localized heating in the sample to cause Lamb waves, a receiver for receiving the Lamb waves, an assembly for providing relative movement of the sample, the energy source and the receiver along a portion of the length of the weld seam, a computer readable medium for storing one or more signals generated by the receiver, and a model for correlating the one or more signals generated by the receiver to empirical data.

The present invention investigates the sensitivities of different Lamb waves in LEU signals to varying WPDs. Transmission coefficients of selected Lamb waves are calculated based on CWT of individual LEU signals. A neural network is developed to use the transmission coefficients of selected Lamb waves and the LEU signal energy to predict WPDs in thin structures.

These and other objects, features and advantages of the present invention will become more apparent upon reading the following specification in conjunction with the accompanying drawing figures.

DETAIL DESCRIPTION OF THE INVENTION

Figure 1A:
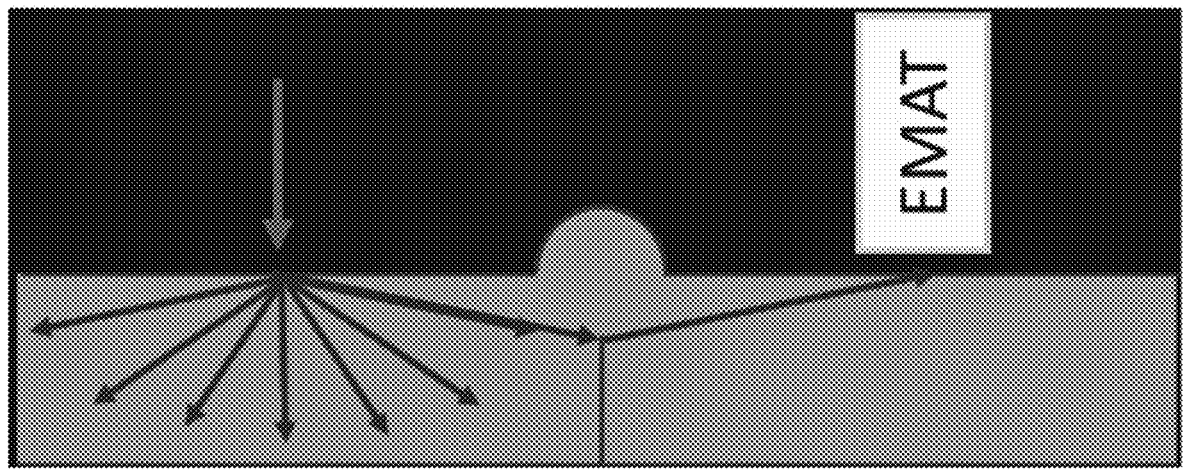
FIGS. 1(a) and (b) illustrate the LEU technique used for WPD inspection in thick FIG. 1(a) and thin FIG. 1(b) structures.
Figure 1B:
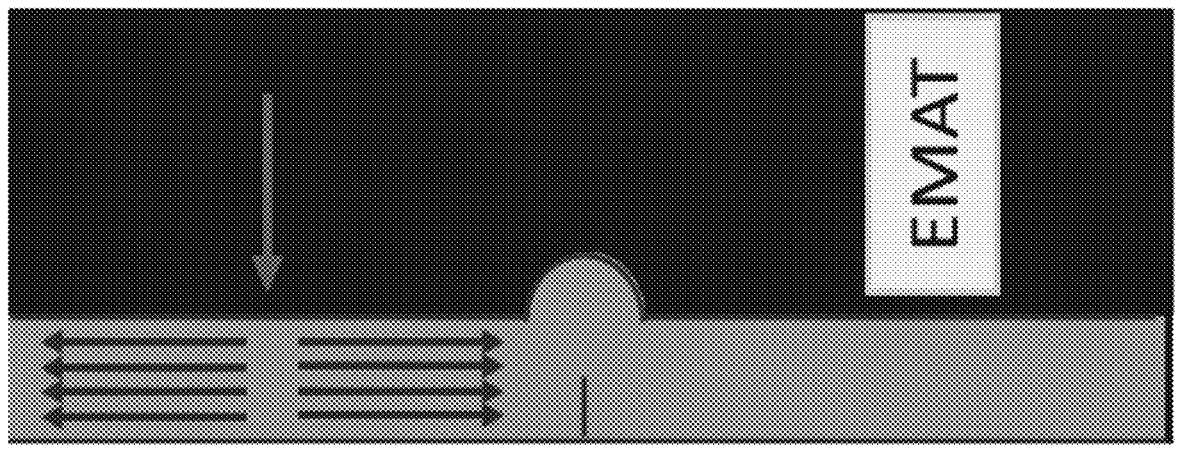

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

The present invention includes systems and methods of high speed measurement of weld penetration depths in thin structures using transmission coefficients of laser-generated Lamb waves and a neural network. As presented, first welds of different penetration depths are manufactured using gas metal arc welding (GMAW). Second, welded samples are inspected nondestructively using the LEU technique. Third, welded samples are cut-checked to measure WPDs at LEU inspected locations. Fourth, CWT of LEU signals is used to calculate transmission coefficients of different Lamb waves. Fifth, Lamb waves whose transmission coefficients are sensitive to varying WPDs are selected. Sixth, transmission coefficients of the selected Lamb waves are used to develop a neural network to predict WPDs in thin structures. Thereafter considerations regarding implementation of the present invention are outlined.

Sample Preparation

Figure 2:
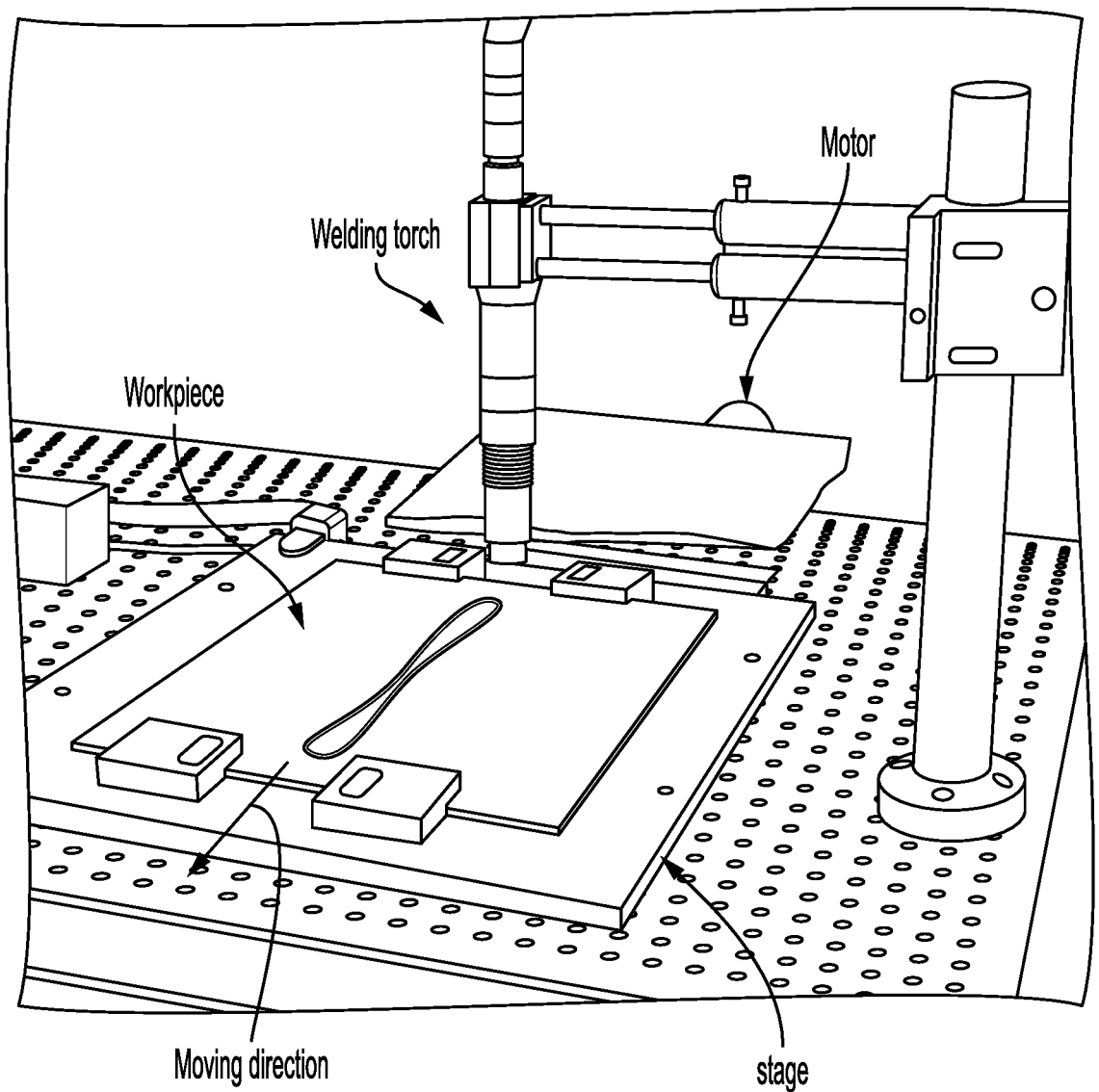
FIG. 2 illustrates an exemplary welding setup.

Gas metal arc welding (GMAW) was used to manufacture welds of varying WPDs. FIG. 2 shows the welding setup used in this work. Two plates are positioned butt-to-butt on a step motor driven stage, above which a welding torch is held perpendicularly. During the welding process, the stage moves beneath the welding torch, and a weld is produced along the butt joint between the two plates. This system uses a Miller Pulstar 450 welder, which provides an interface to control arc voltage and wire feed rate (WFR) of the consumable electrode through external analog signals. A microcontroller module changes the arc voltage, WFR, and the stage speed during the welding process to produce varying WPDs.

Six eight inch long butt welds joining 2.9 mm thick A36 steel plates were manufactured in this configuration. FIGS. 3(a)-(d) show the profiles of arc voltage and WFR used to control the welding processes. The profiles were designed and pretested to produce a wide range of WPDs along each weld.

TABLE 1 lists the profile selection for producing each weld. In this setup, welds 1-4 were manufactured first, which were used to develop a neural network. Welds 5-6 were manufactured later, which were used to provide additional tests of the developed neural network.

TABLE 1

Profile Selection For Each Weld

Figure 3A:
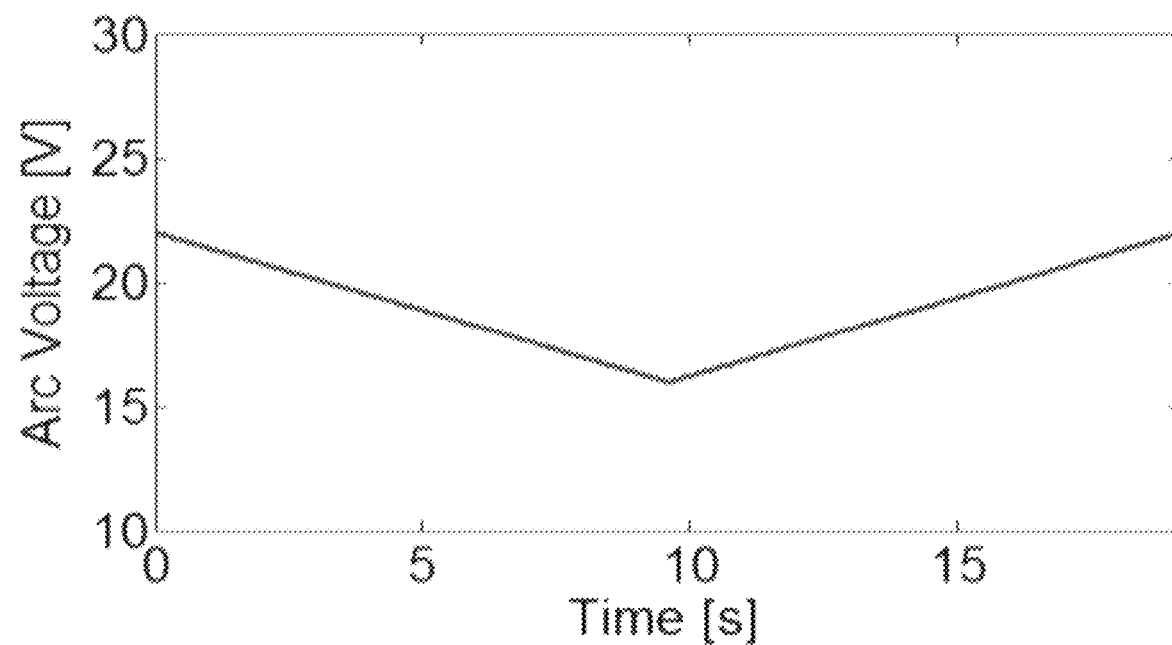
FIGS. 3(a)-(d) are graphs illustrating profiles of arc voltage and WFR.
Figure 3B:
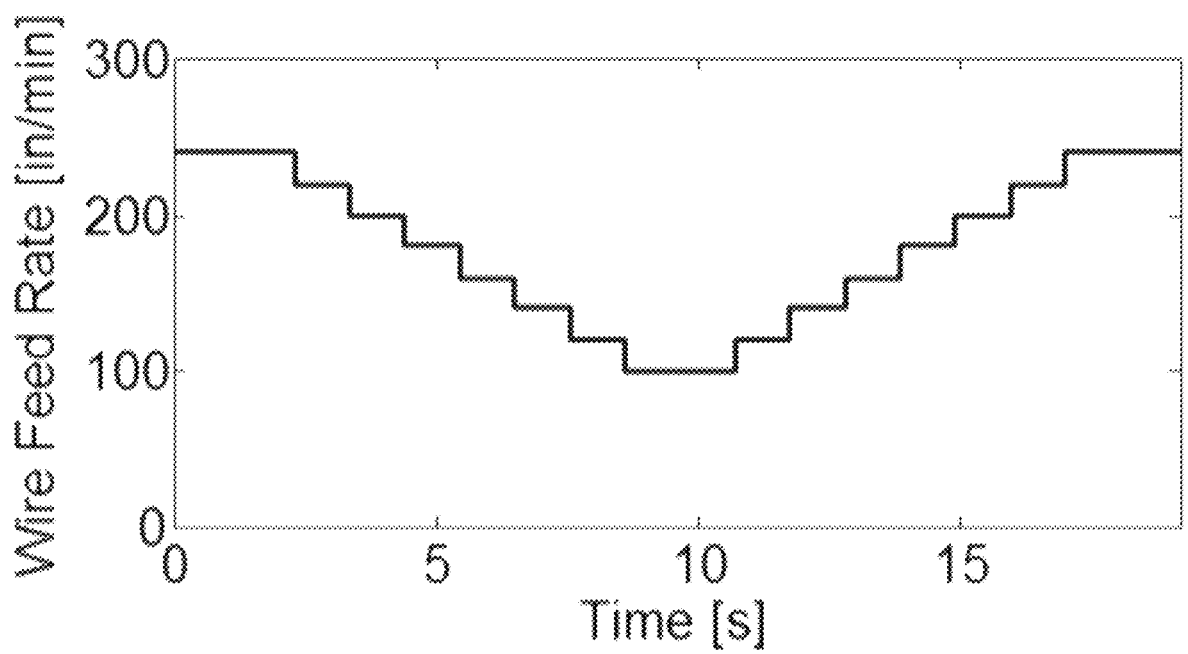
Figure 3C:
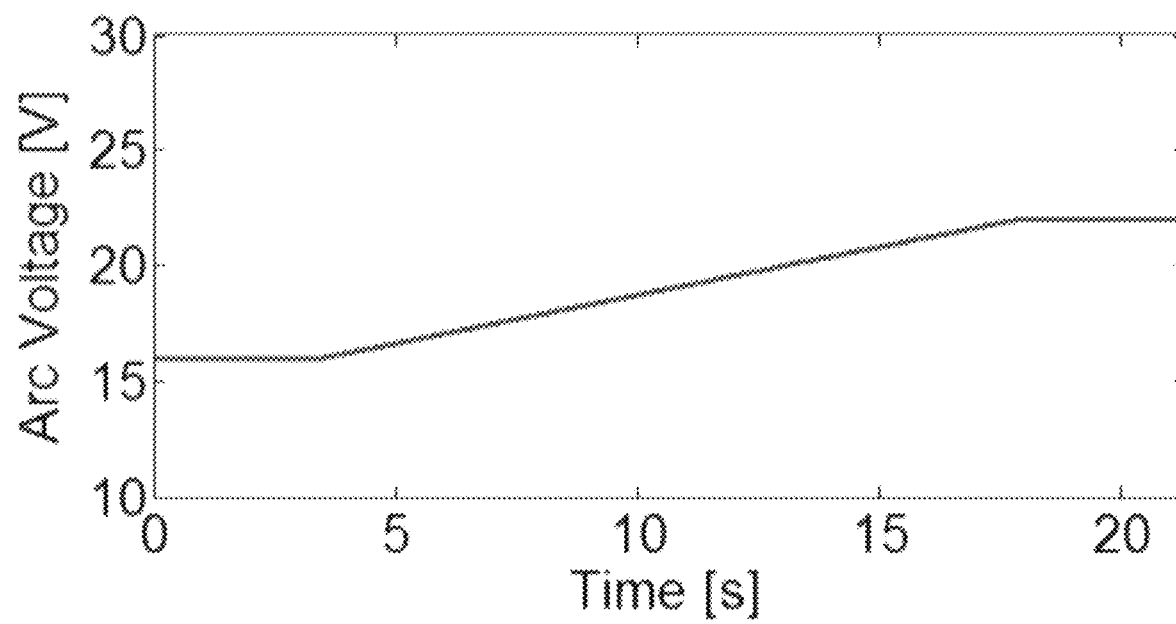
Figure 3D:
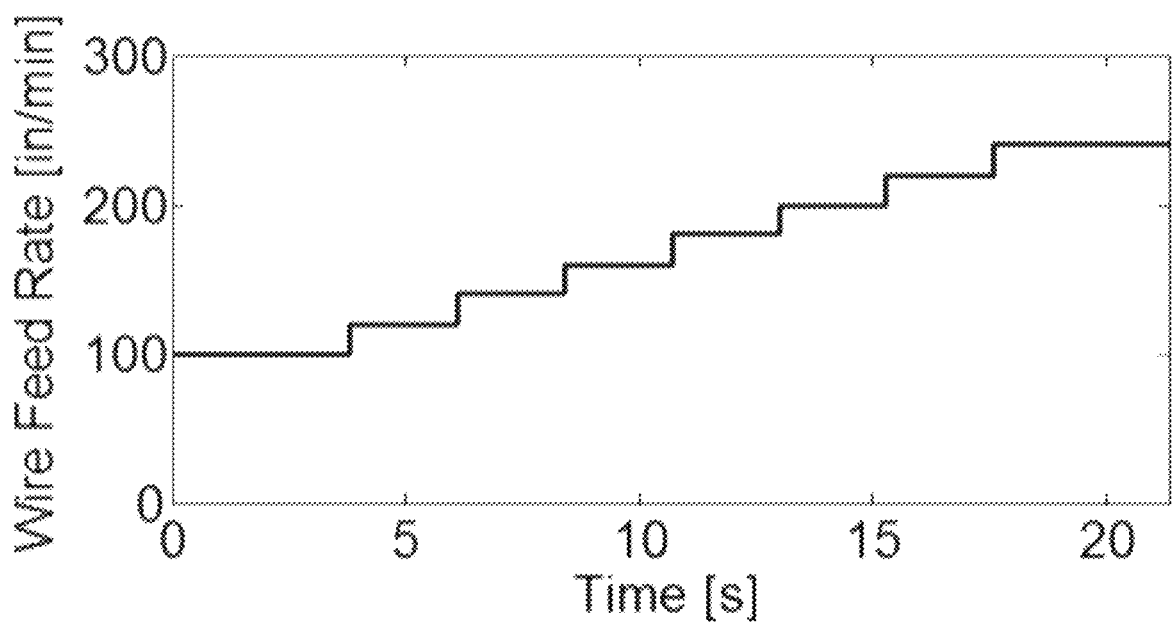

| Weld No. | Length (inches) | Stage Speed (inches/min.) | FIG. Showing Arc Voltage | FIG. Showing WFR |
|---|---|---|---|---|
| 1 | 8 | 25 | FIG. 3(a) | FIG. 3(b) |
| 2 | 8 | 22.5 | FIG. 3(a) | FIG. 3(b) |
| 3 | 8 | 22.5 | FIG. 3(a) | FIG. 3(b) |
| 4 | 8 | 25 | FIG. 3(a) | FIG. 3(b) |
| 5 | 8 | 22.5 | FIG. 3(a) | FIG. 3(b) |
| 6 | 8 | 22.5 | FIG. 3(c) | FIG. 3(d) |

LEU Inspection

Figure 4:
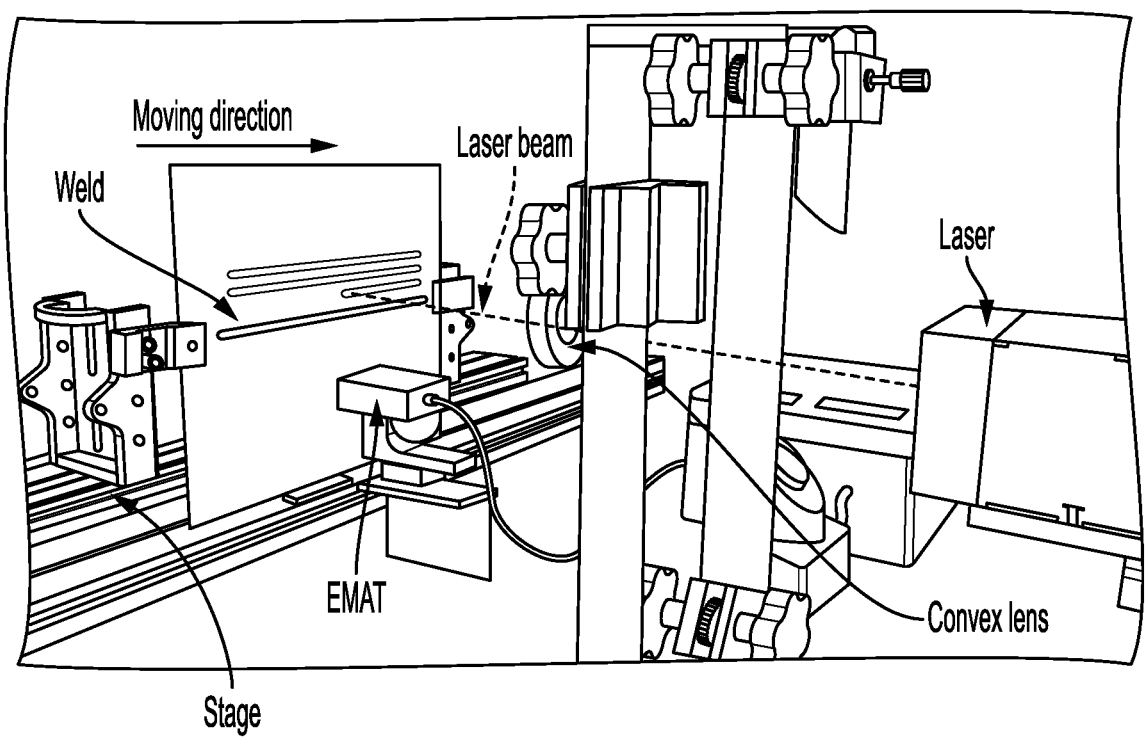
FIG. 4 is an exemplary LEU inspection system.

After the welded samples were manufactured, they were first nondestructively inspected using the LEU technique. FIG. 4 shows the inspection setup. The LEU system comprises an Nd:YAG pulsed laser, a custom designed EMAT, a 1-directional moving stage, a high speed acquisition card, and a control unit.

The sample was held vertically on the moving stage, with the weld seam facing the laser. The laser beam was focused to a point source of 0.5 mm in radius above the weld seam to excite ultrasounds. The EMAT was attached to the sample through its built-in magnet to receive ultrasounds from below the weld seam. The laser-to-EMAT distance was 64 mm, and the laser-to-weld distance was 47 mm. During the inspection, the sample moved with the stage, allowing the laser/EMAT pair to inspect 91 locations at increments of 2 mm along each weld.

At each location, the laser fired 16 times, and the acquired signals were averaged later to improve the signal to noise ratio (SNR). The laser power was set to 115 mJ/pulse, which excited ultrasounds in the ablative regime. The EMAT has a bandwidth from 0.5 MHz to 2.0 MHz. The sampling frequency was set to 12.5 MHz. The received LEU signals were stored in PC for signal processing later. A reference signal was acquired by inspecting a defect-free plate with the same laser-to-EMAT distance. The reference signal will be used to calculate transmission coefficients later.

Cut Check

After the nondestructive inspection, the welds were cut along weld seams to measure WPDs at LEU inspected locations. It was very difficult to cut accurately along the middle line of weld seams. Therefore, the welds were first cut along a line 2 mm off the middle line, and the rest was grinded off using grit 80 sandpapers later.

Figure 5:
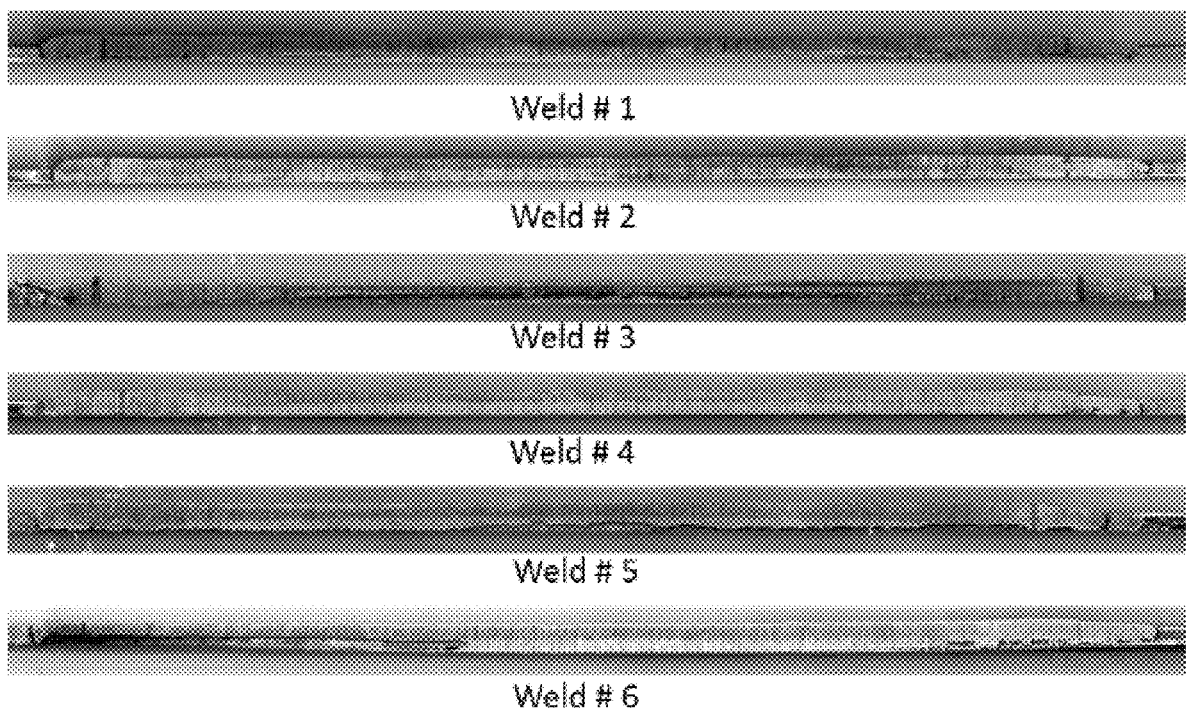
FIG. 5 illustrates scanned images of welds 1-6.
Figure 6A:
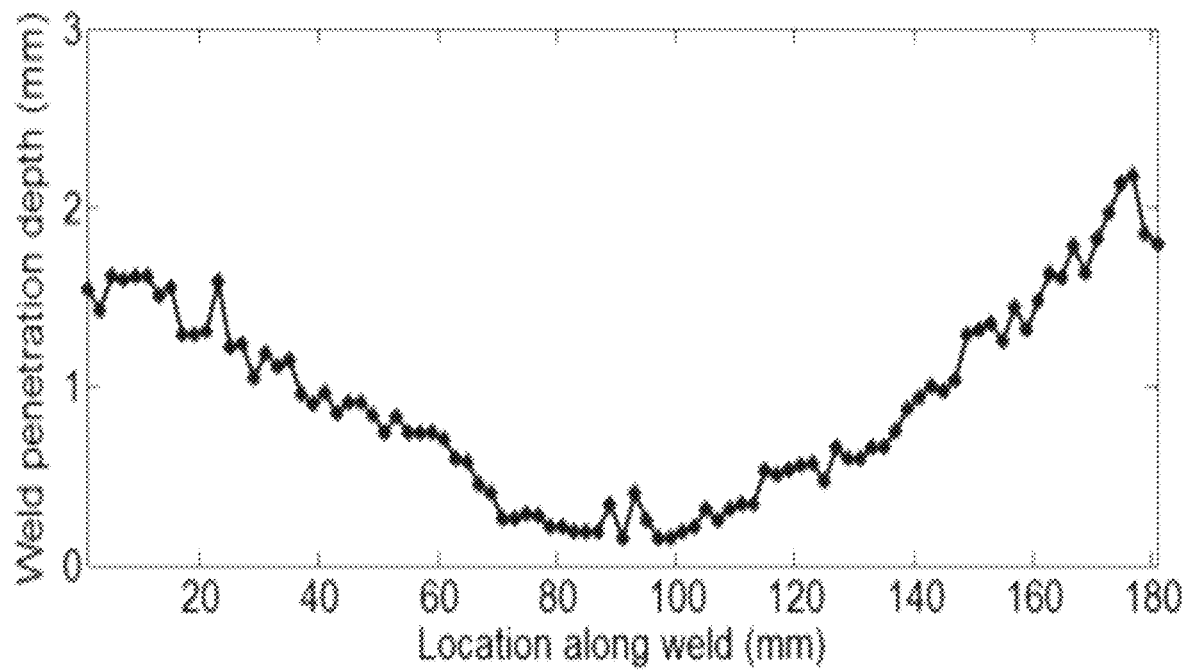
FIGS. 6(a)-(f) are graphs illustrating cut-check measured WPDs.
Figure 6B:
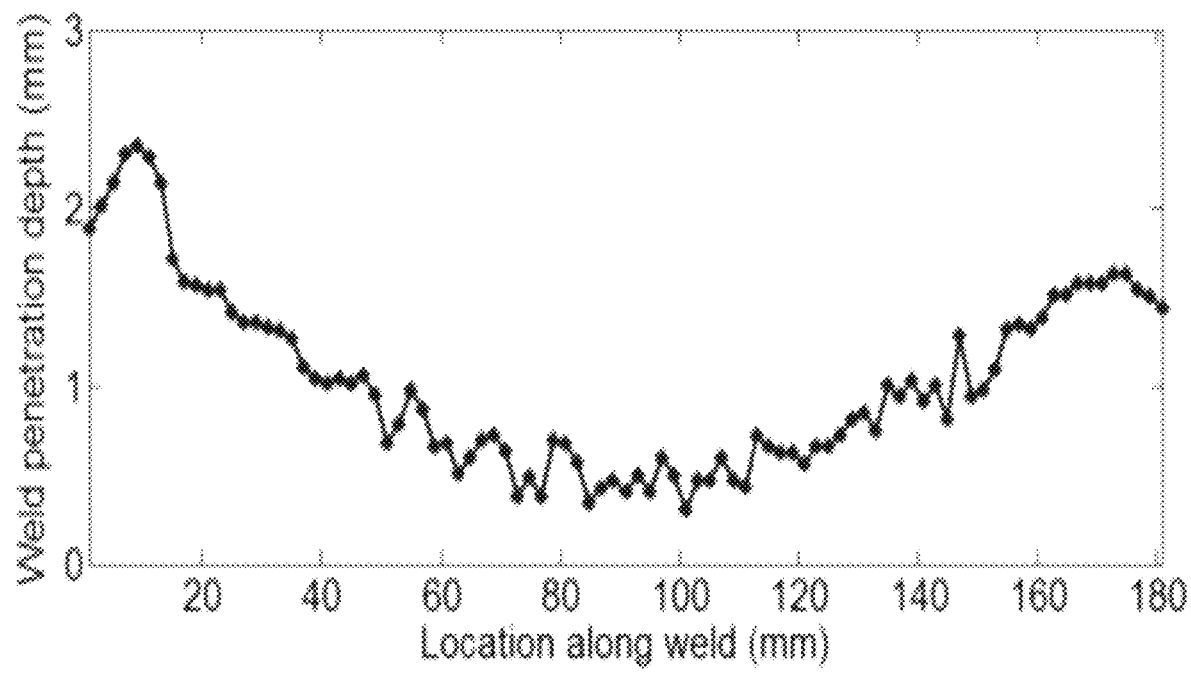
Figure 6C:
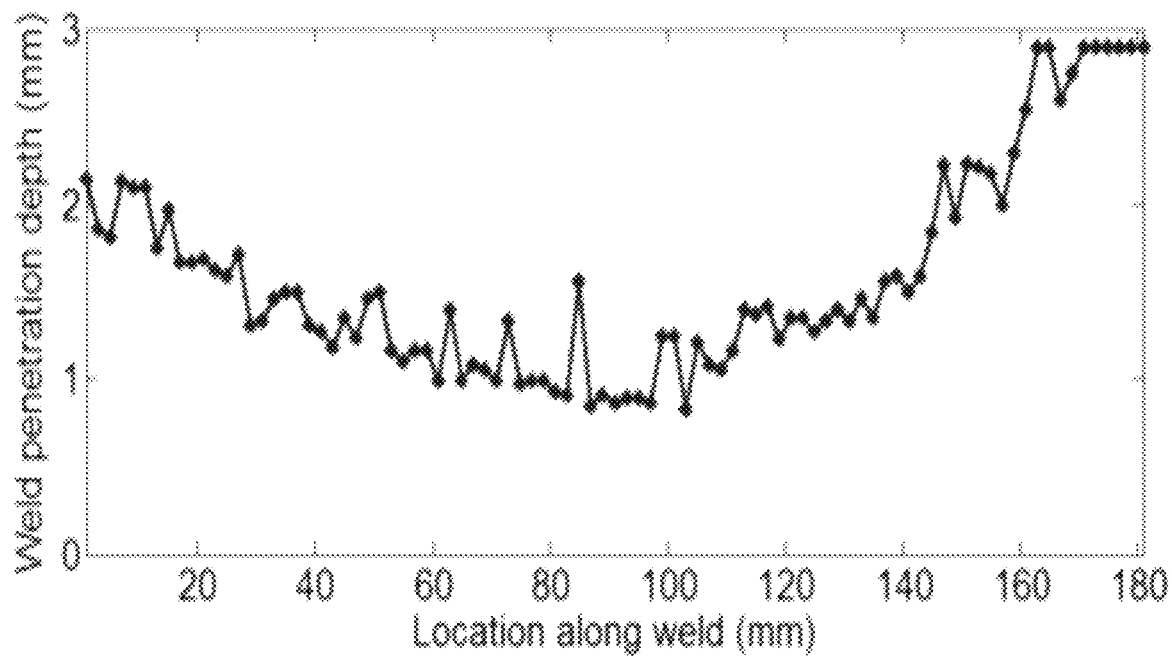
Figure 6D:
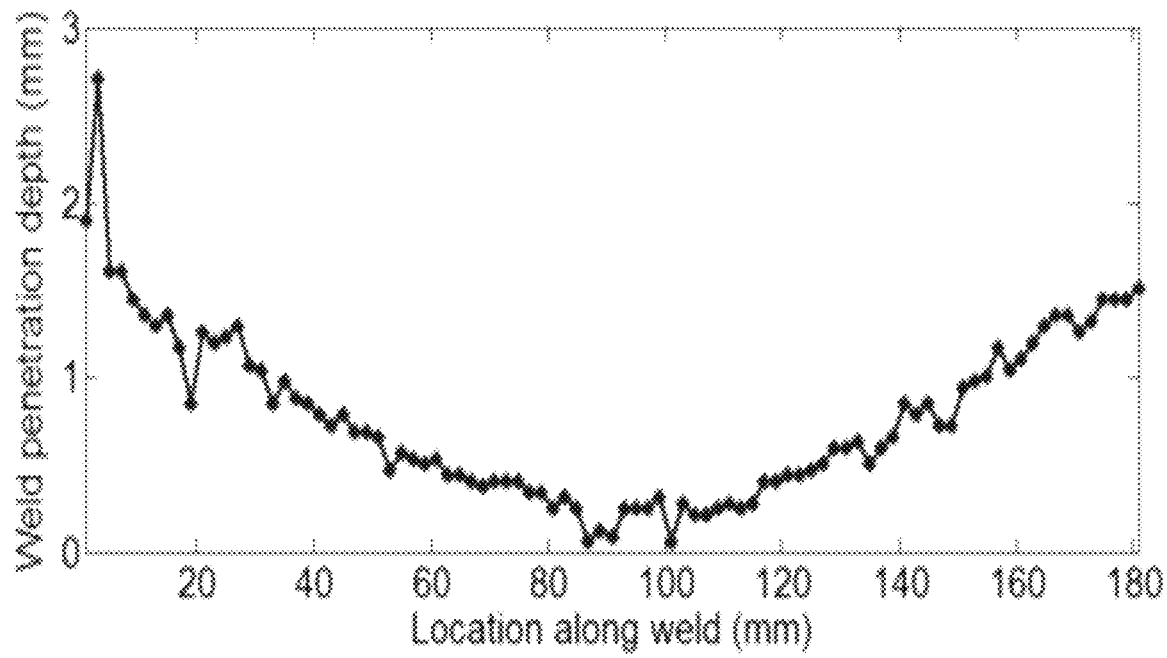
Figure 6E:
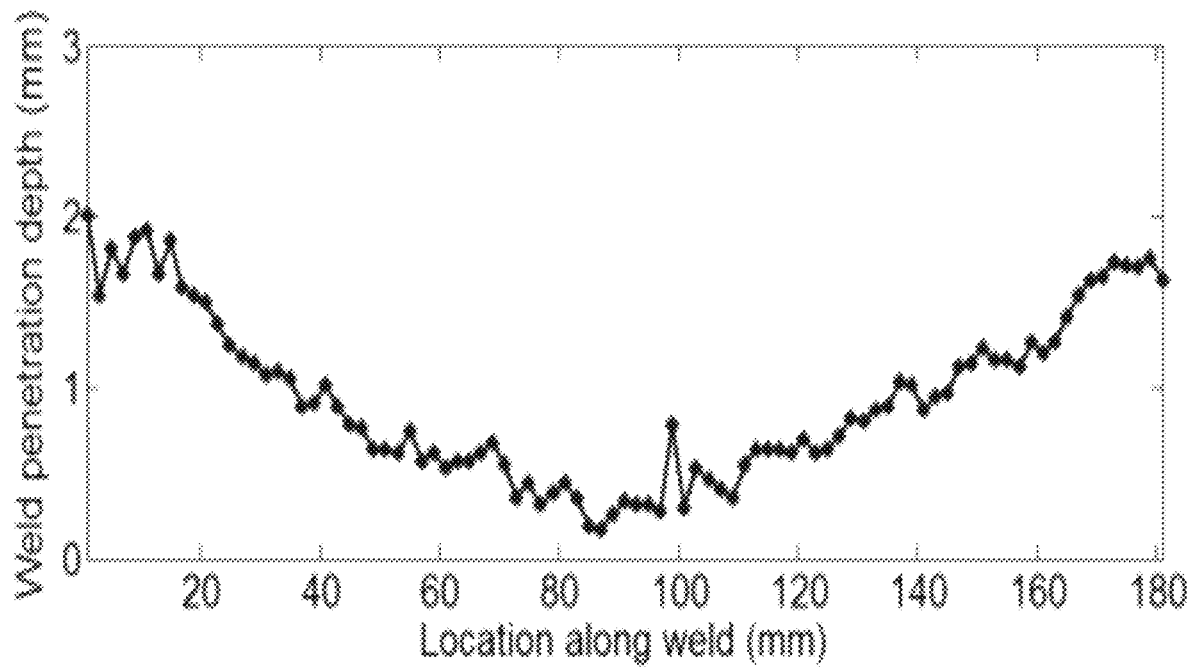
Figure 6F:
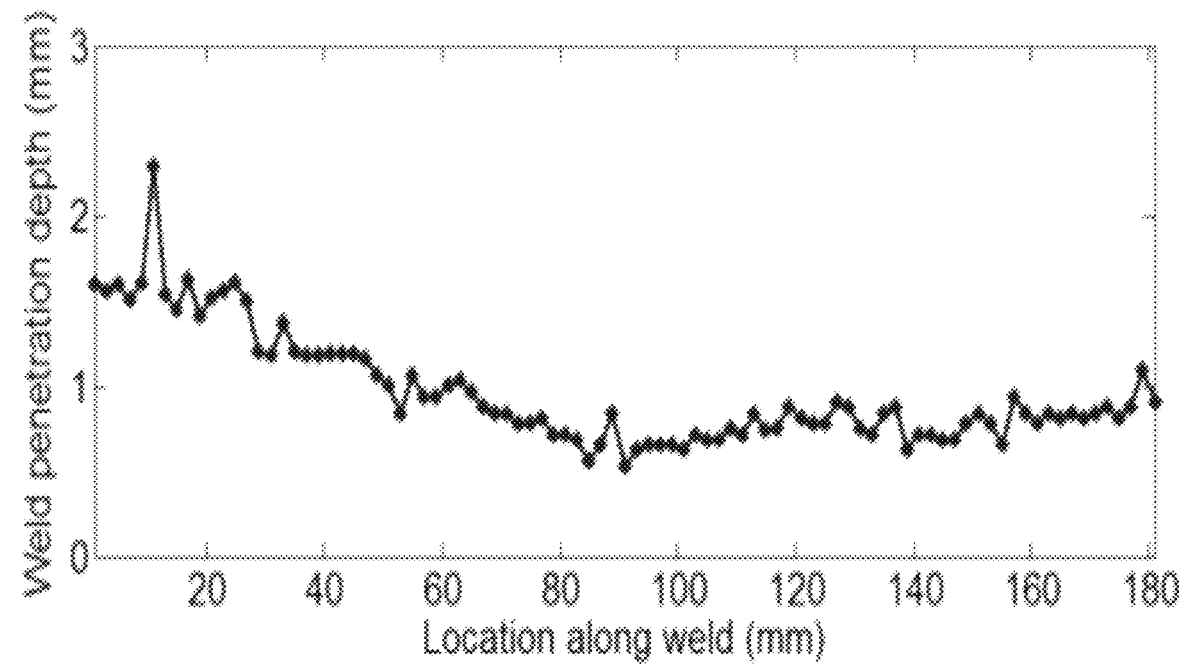

Next, the cross-sections were etched using 5% sulfuric acid to make the boundaries between the weld material and the base material clear to see. Finally, the samples were scanned using an optical scanner with a 1200 dpi resolution. FIG. 5 shows the scanned images of the six welds. WPDs were measured from the scanned images using MATLAB Image Toolbox. FIGS. 6(a)-(f) show the cut-checked WPDs for the six samples. Profiles in FIG. 3 proved to successfully produce varying WPDs in the samples. Welds 1-4 contain zero to full WPDs, which are suitable to use as the training data.

Calculation Of Transmission Coefficients

The acquired LEU signals contain multiple Lamb wave modes, which are overlapping in both time and frequency domains. CWT converts the LEU signals to their time-frequency domain representations, from which different Lamb waves can be separated.

Figure 7:
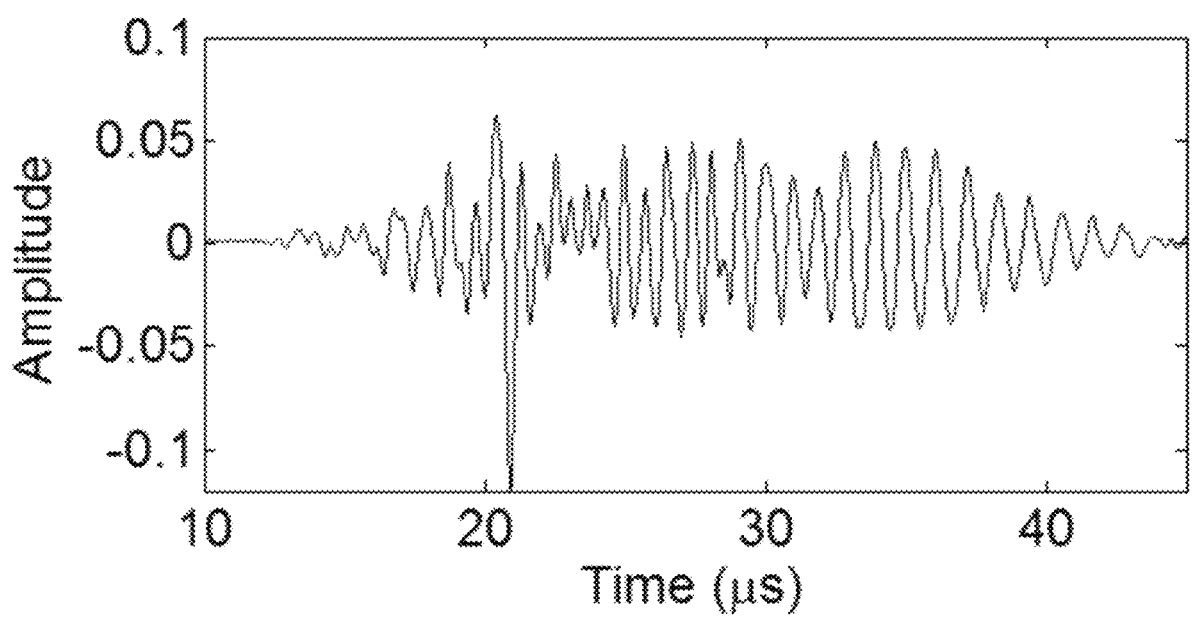
FIG. 7 is a graph of the reference signal.
Figure 8A:
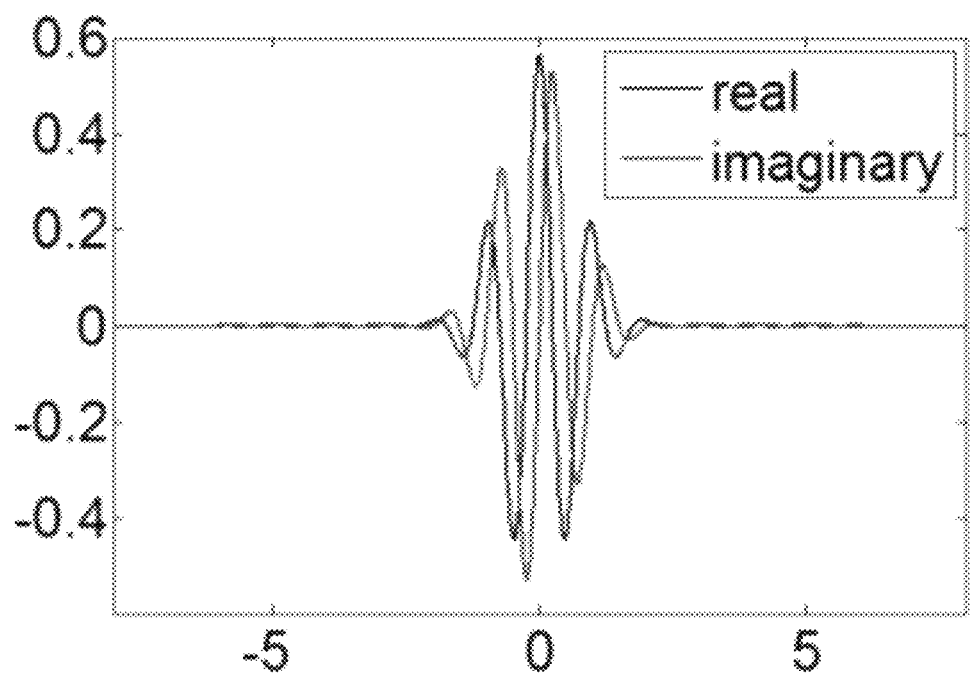
FIGS. 8(a)-(b) are graphs of mother wavelets used for CWT; (a) Complex-valued Morlet (Fb=1, Fc=1), and (b) Complex-valued Morlet (Fb=6, Fc=1).
Figure 8B:
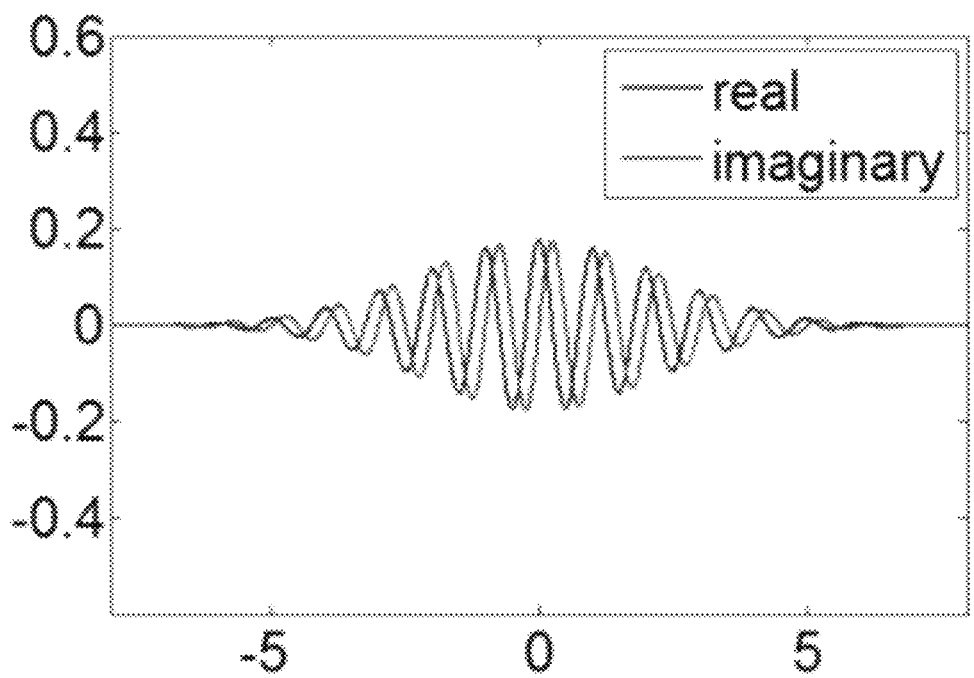
Figure 9A:
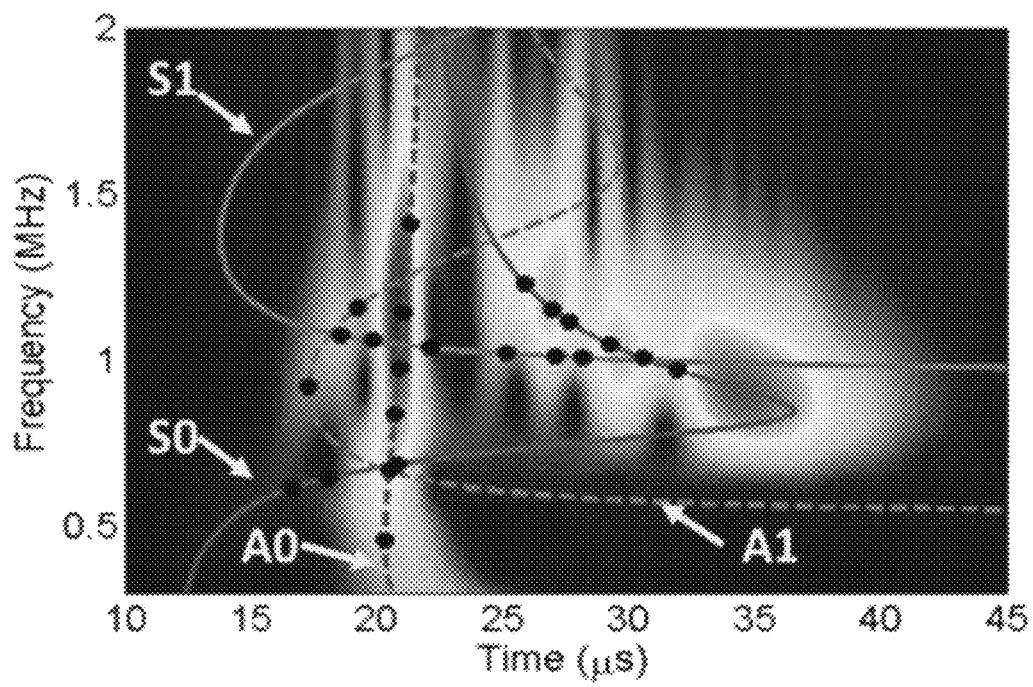
FIGS. 9(a)-(b) are CWT plots of reference signal using two different mother wavelets; (a) CWT using FIG. 8(a), and (b) CWT using FIG. 8(b).
Figure 9B:
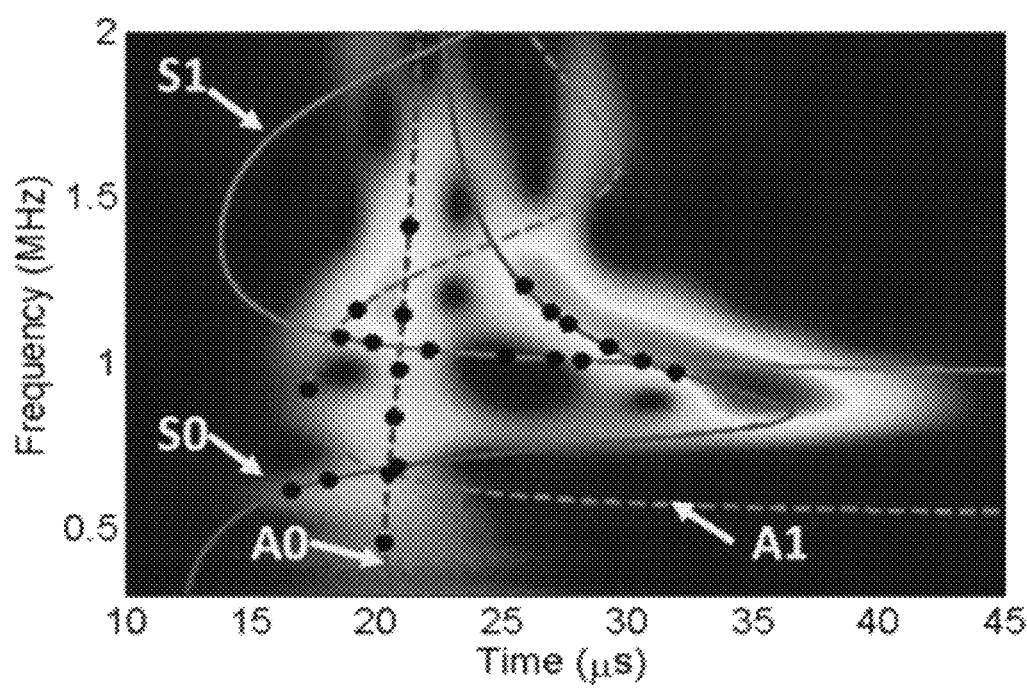

FIG. 7 shows the acquired reference signal. Based on the wave form of the LEU signal, two versions of complex-valued Morlet wavelets were used as the mother wavelets, which are shown in FIGS. 8(a)-(b). FIGS. 9(a)-(b) show the CWT plots of the reference signal using the two wavelets. Theoretical dispersive curves corresponding to arrival times of different Lamb waves are superimposed to the two CWT plots, which help to identify different Lamb waves present in the LEU signal.

The LEU signal contains strong A0 and S0 modes. The first wavelet is good at identifying A0 mode, and the second wavelet is good at identifying S0 mode. The A0 and S1 modes are not as outstanding in the time-frequency domain because of the limited resolution of CWT. Lamb waves cannot be completely separated in the time-frequency domain. For example, in some regions dispersive curves of different Lamb waves are close to or even intersect with each other. The A1 and S1 modes are also of interest even though they are obscured by the strong A0 and S0 modes in the received signals.

As used herein, CWT coefficients corresponding to different Lamb waves were used to calculate their transmission coefficients, as defined in Eq. 1:

$$C_{tr} = CA_d / CA_0 \qquad (1)$$

where $CA_d$ is the CWT coefficient amplitude of a Lamb wave when the WPD equals d, and $CA_0$ is the CWT coefficient amplitude of the same Lamb wave in the reference signal. CWT coefficients of Lamb waves were located with help of the superimposed theoretical dispersive curves. In implementation, the root mean square of local CWT coefficient amplitudes of each Lamb wave of interest was used to calculate the transmission coefficient. Mother wavelets were selected carefully since they have different capabilities to identify different Lamb waves.

Selection Of Sensitive Lamb Waves

An objective of the present invention is to use transmission coefficients of Lamb waves to predict WPDs in thin structures. The LEU signals contain broadband and multimodal Lamb waves. Therefore, it is necessary to select Lamb waves which are sensitive to varying WPDs. For the 364 LEU signals acquired from welds 1-4, scatter plots of transmission coefficients versus cut-checked WPDs were plotted for different Lamb waves.

Some of the scatter plots exhibited patterns, which means the corresponding Lamb waves are sensitive to varying WPDs. Some of the scatter plots were random, which means the corresponding Lamb waves not sensitive to varying WPDs.

Figure 10:
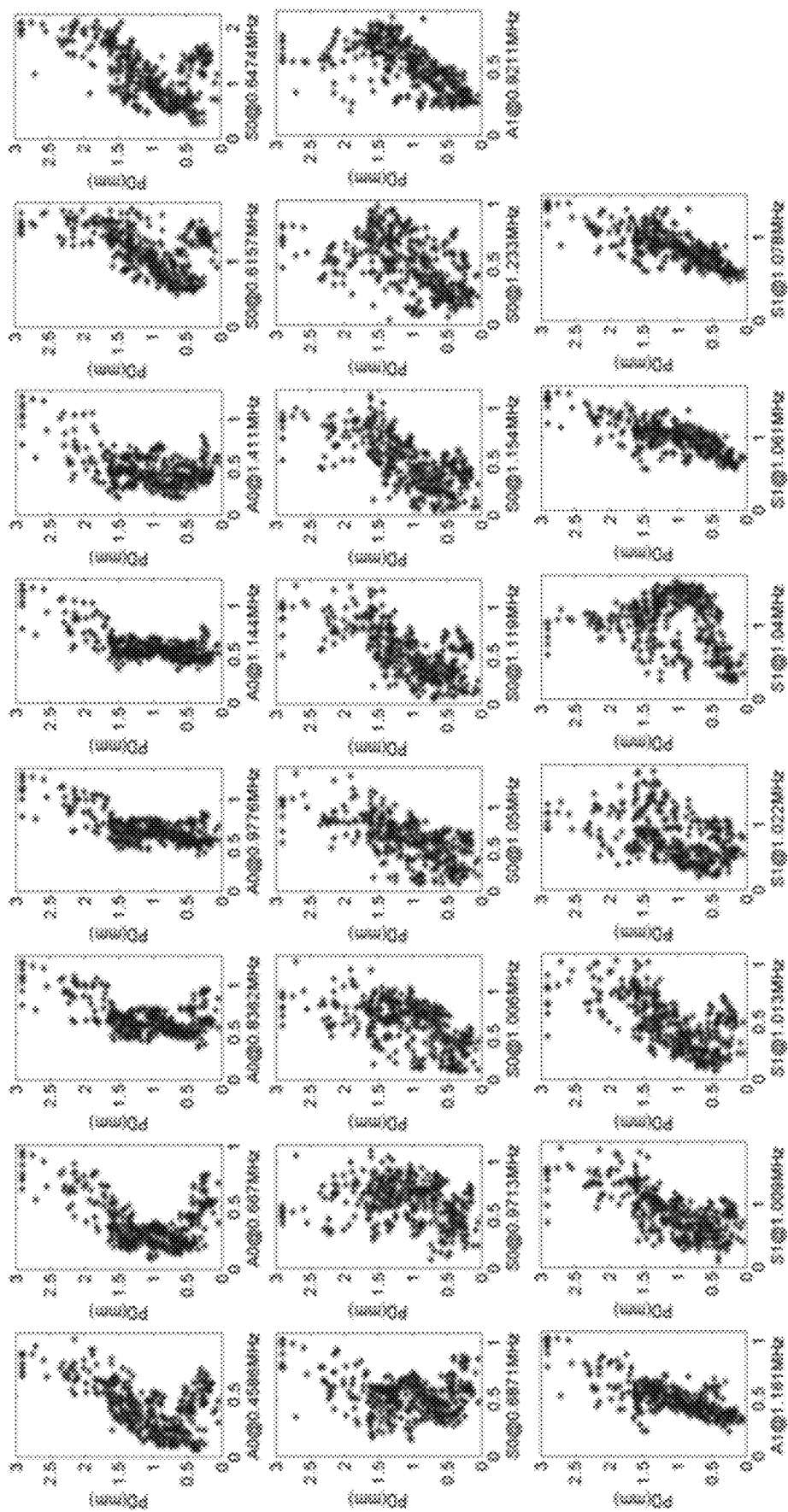
FIG. 10 shows scatter plots of selected Lamb waves.

Finally, 23 sensitive Lamb waves were selected, and are listed in TABLE 2. The selected Lamb waves were plotted as black dots in FIGS. 9(a)-(b). TABLE 2 also lists the mother wavelets selected to calculate their transmission coefficients. Scatter plots of transmission coefficients versus cut-checked WPDs for the selected Lamb waves are shown in FIG. 10. For some Lamb waves, their transmission coefficients exceed 1, which can be interpreted by mode conversions occurring at the welds.

TABLE 2

Lamb Waves Selected To Calculate Transmission Coefficients

| Lamb Mode | Frequency (MHz) | (Fb, Fc) | Lamb Mode | Frequency (MHz) | (Fb, Fc) | Lamb Mode | Frequency (MHz) | (Fb, Fc) |
|---|---|---|---|---|---|---|---|---|
| A0 | 0.4586 | (1, 1) | S0 | 0.6157 | (1, 1) | A1 | 0.9211 | (1, 1) |
|  | 0.667 | (1, 1) |  | 0.6474 | (1, 1) |  | 1.161 | (1, 1) |
|  | 0.8362 | (1, 1) |  | 0.6871 | (6, 1) | S1 | 1.009 | (6, 1) |
|  | 0.9776 | (1, 1) |  | 0.9713 | (6, 1) |  | 1.013 | (1, 1) |
|  | 1.144 | (1, 1) |  | 1.006 | (6, 1) |  | 1.022 | (1, 1) |
|  | 1.411 | (1, 1) |  | 1.05 | (6, 1) |  | 1.04 | (6, 1) |
|  |  |  |  | 1.119 | (6, 1) |  | 1.061 | (6, 1) |
|  |  |  |  | 1.154 | (6, 1) |  | 1.078 | (6, 1) |
|  |  |  |  | 1.233 | (6, 1) |  |  |  |

Figure 11:
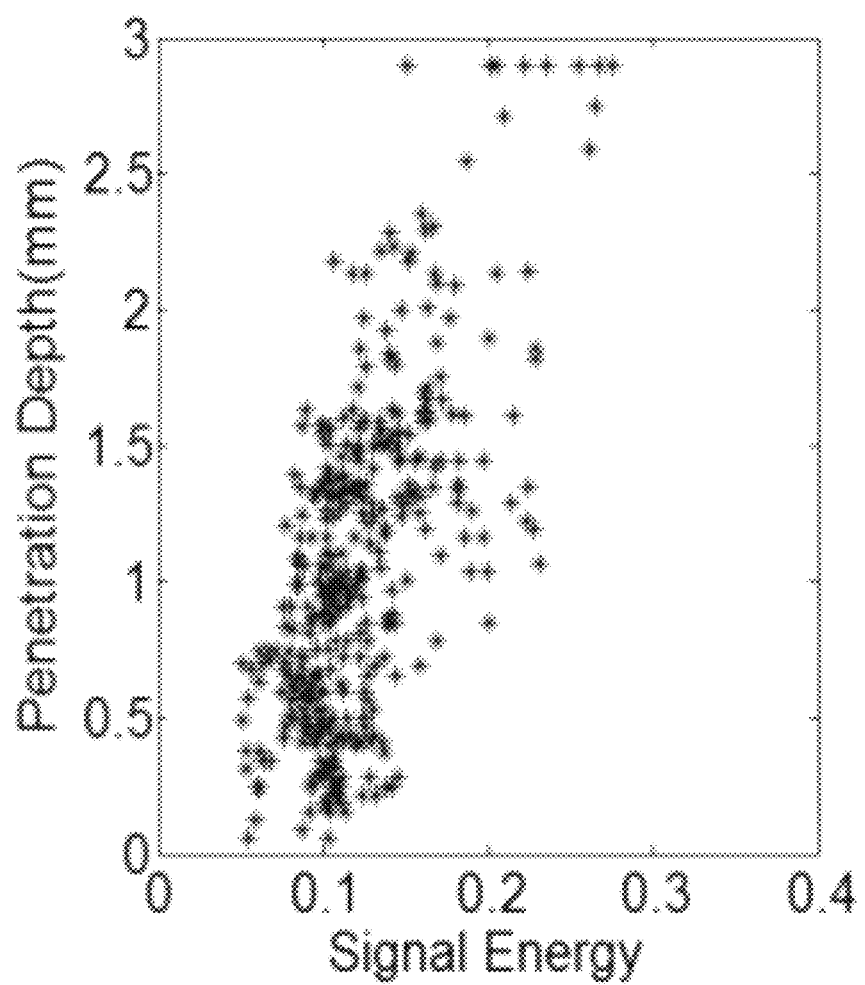
FIG. 11 is a scatter plot of LEU signal energies vs. WPDs.

In addition to transmission coefficients of 23 selected Lamb waves, the LEU signal energy calculated using sum of square was found to be also sensitive to varying WPDs, as shown in FIG. 11.

The scatter plots in FIGS. 10 and 11 are noisy, which may be caused by many reasons. First, in addition to the WPD, the other weld dimensions, such as weld reinforcement height, bead width, and the seam width between two plates, are also wildly varying at different inspected locations. Second, the cut check measurement processes may introduce errors. Third, the LEU system is unstable over time.

Figure 12:
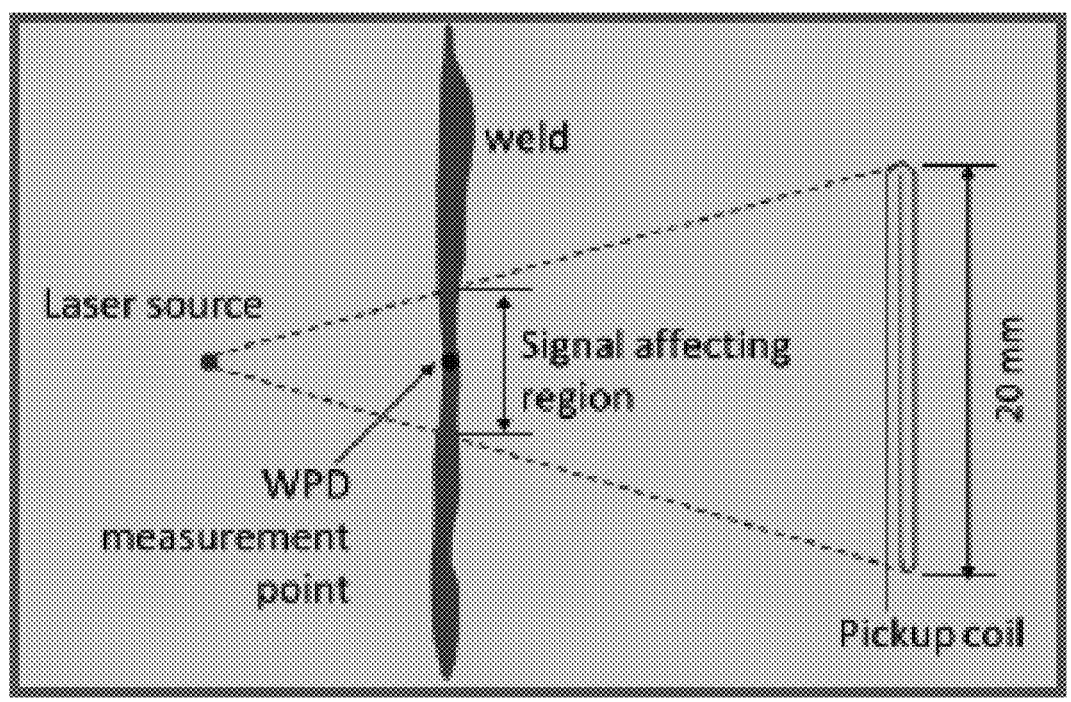
FIG. 12 is a layout of laser and EMAT relative to weld seam.

Another reason is illustrated in FIG. 12. Because the EMAT pickup coil is 20 mm long in the weld seam direction, the received signals are affected by WPDs of a region along the weld. However, cut-check only measures the WPD at the center of this signal affecting region. WPDs within the signal affecting region may vary a lot.

Artificial Neural Network

After the sensitive Lamb waves were selected, using their transmission coefficients to predict WPDs became a data fitting problem. Transmission coefficients of some Lamb waves exhibited nonlinear relationships with WPDs. Among different nonlinear data fitting techniques, such as nonlinear regression and stochastic approximation, artificial neural network (ANN) proves the capability to provide equally comparable solutions with some additional advantages, such as fault-tolerance through the large number of connections, parallel implementations that allow fast processing, and on-line adaption which allows continuous improvements. ANN is selected for this work because of its fault-tolerance capability.

Figure 13:
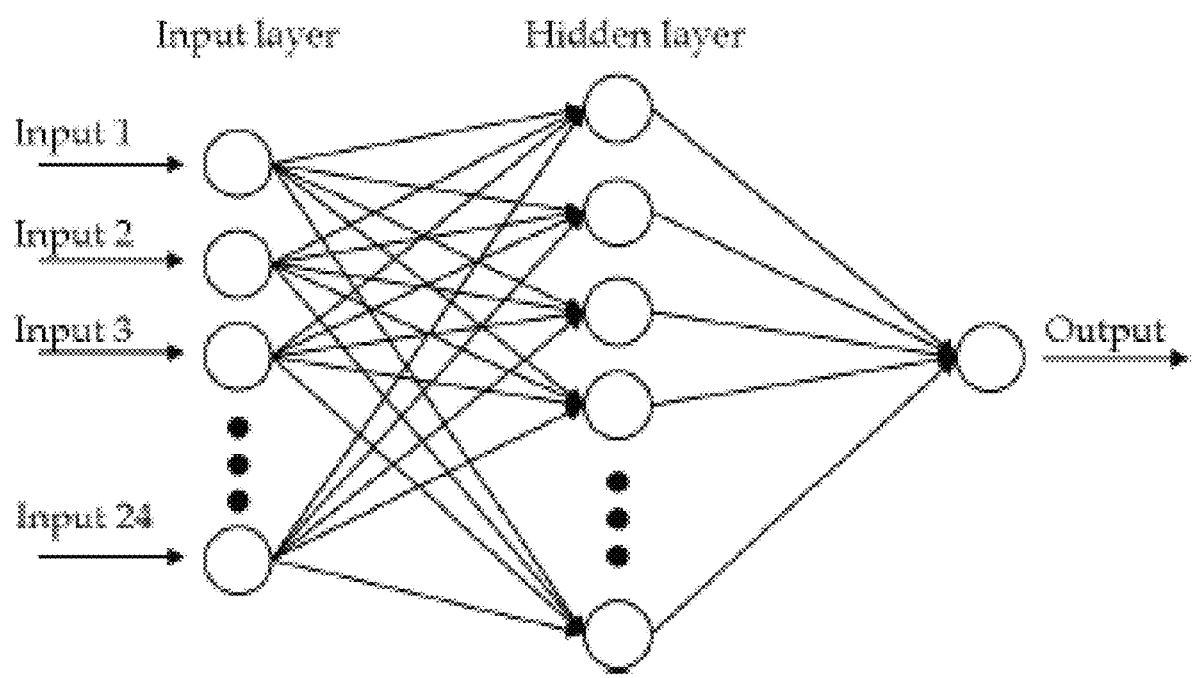
FIG. 13 is an exemplary structure of a neural network.

FIG. 13 shows the structure of an exemplary ANN, which is a two-layer feed-forward data fitting network. The input layer has 24 nodes accepting transmission coefficients of 23 selected Lamb waves and the LEU signal energy, and the output layer has one node yielding predicted WPDs. The Universal Approximation Theorem (UAT) states that a single hidden layer perceptron network with a sufficiently large number of neurons can approximate any continuous function arbitrarily close. This ANN contains ten hidden sigmoid neurons, which prove to provide a very good approximation later. The output neuron uses the linear function as its activation function.

The network was trained with Levenberg-Marquardt back propagation algorithm using 364 sample points obtained from welds 1-4. The 364 sample points were randomly divided into three groups. 70% of them were used for training directly. 15% of them, which are called validation data, were used to stop the training when their mean square error (MSE) stopped decreasing. The remaining, which are called test data, were used to test the network performance during and after training independently.

Figure 14:
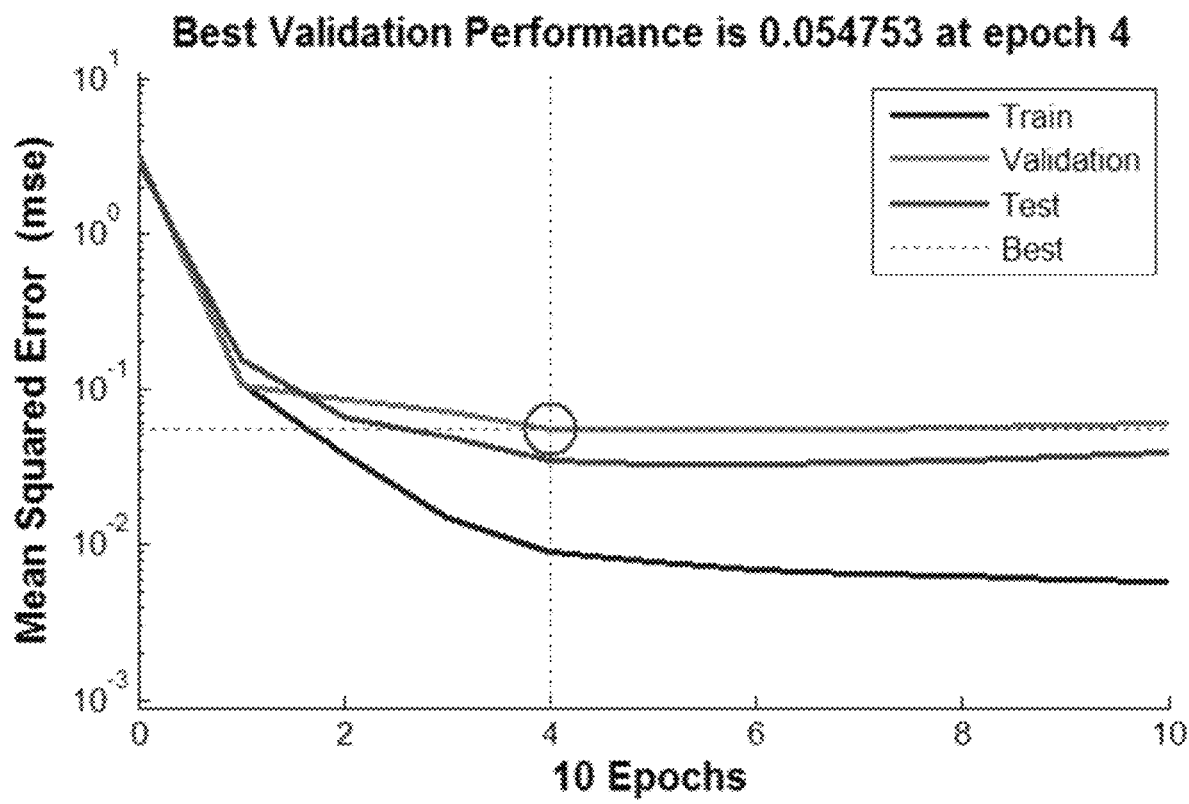
FIG. 14 is a graph of the progress of MSE during training process.

The network performance was evaluated using MSE. The smaller the MSE is, the better the performance is. FIG. 14 shows the progress of MSE of the training, validation and test data during the course of training. The MSE of the training data keeps decreasing as the number of epoch increases. The MSE of the validation data decreases first and increases later.

The best network generalization occurs at Epoch 4, after which the MSE of the validation data starts increasing, that is, the network starts over-fitting. The MSE curve of the test data is very similar to the validation data, which is acceptable. If the test curve increased significantly before the validation curve increased, over-fitting might have started before Epoch 4. At the best epoch, the test data has a smaller MSE than the validation data.

Figure 15:
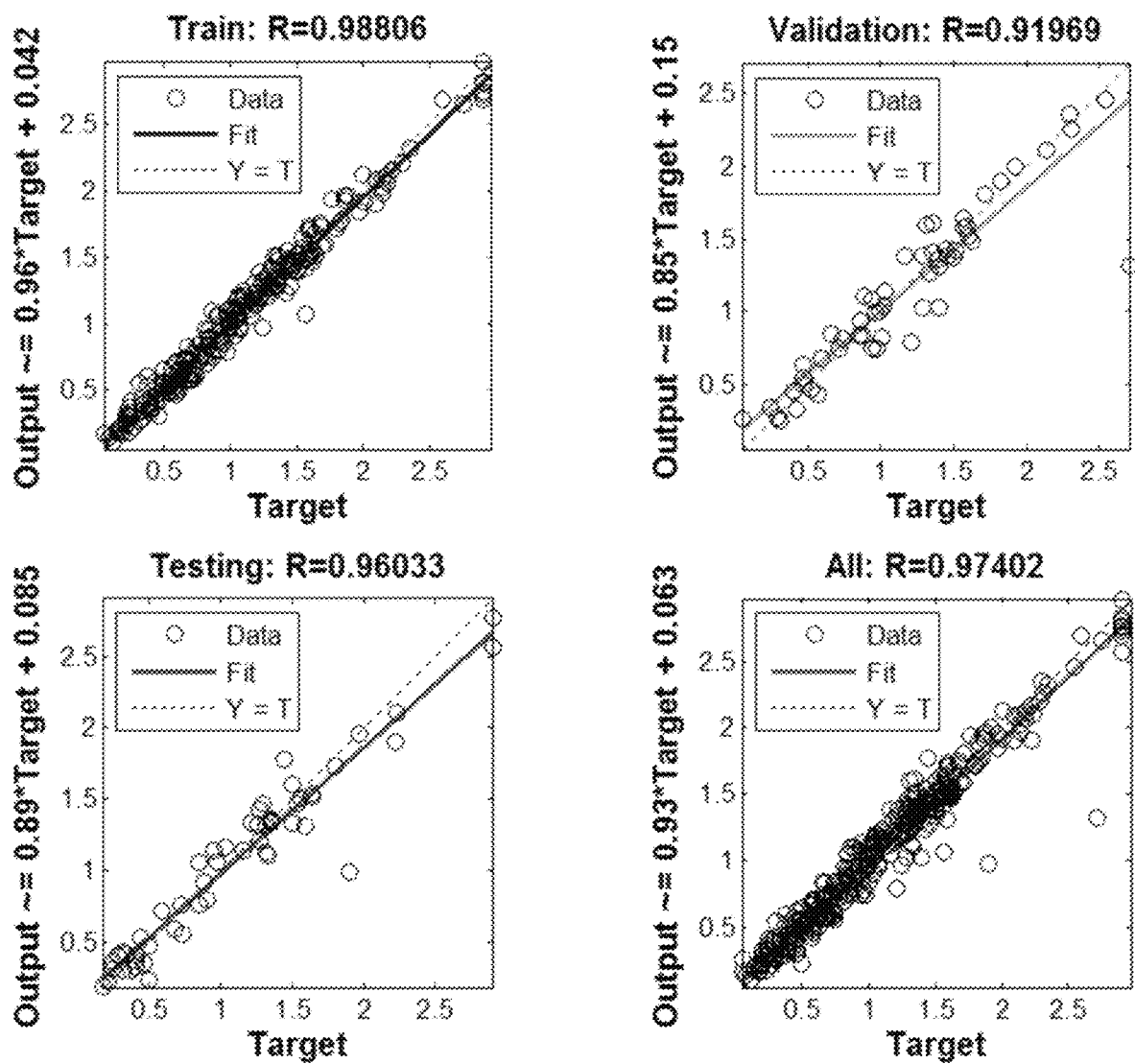
FIG. 15 shows regression plots of network outputs and targets.

FIG. 15 shows the regression plots of network outputs (predicted WPDs) and targets (cut-checked WPDs) for the training, validation and test data at the best epoch. If all the data points fall on the dashed line, the network provides a perfect prediction. The solid line is the linear fitting of the data points.

The closer the solid line is to the dashed line, the better prediction the network provides. The R value measures the correlation between the outputs and targets. An R value close to 1 means a good prediction, and an R value close to 0 means a bad prediction.

The test data has an R value of 0.96033, which means the trained network has a capability to accurately predict WPDs in thin structures.

Figure 16A:
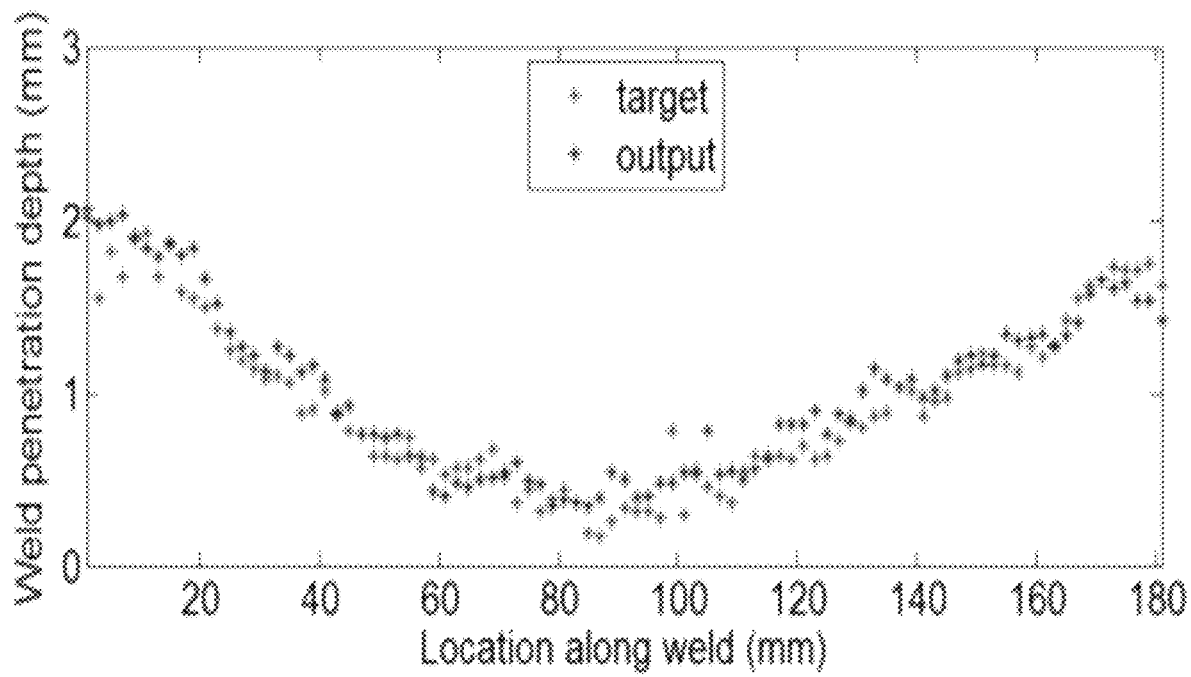
FIGS. 16(a)-(b) plot the comparison of network outputs and targets for (a) weld 5, and (b) weld 6.
Figure 16B:
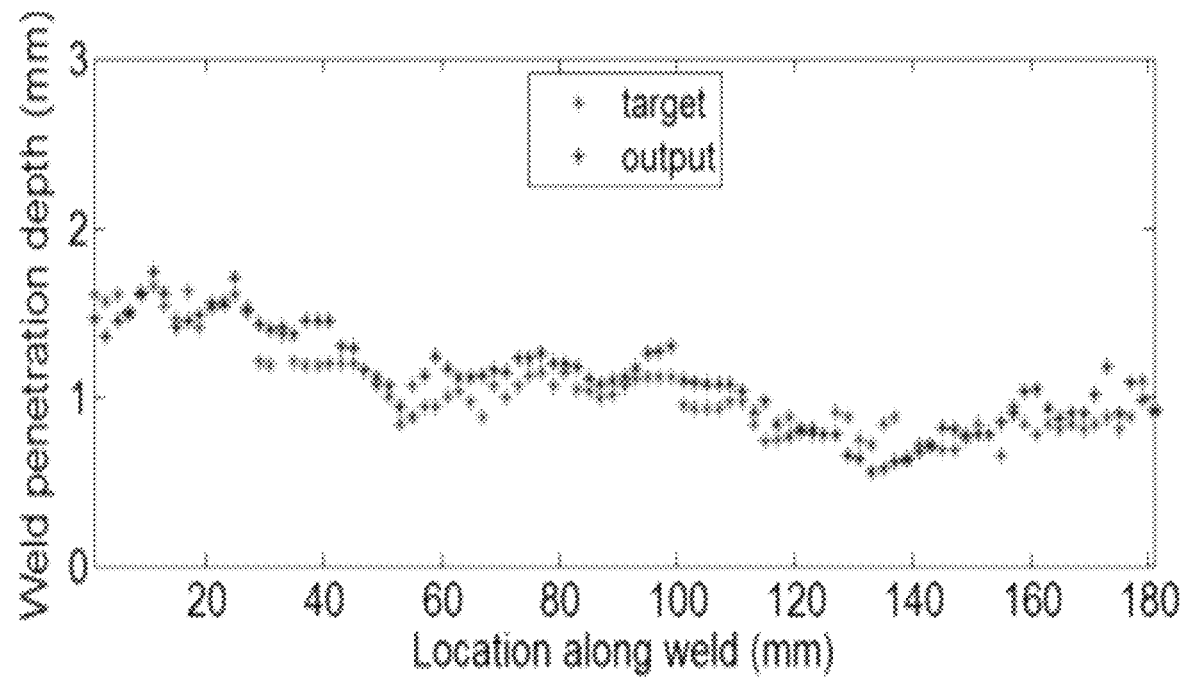

Welds 5 and 6 were not used in the development of the neural network. Therefore, they can provide additional tests of the network. FIG. 16 shows the comparison between the predicted WPDs and the cut-checked WPDs along welds 5 and 6. The predictions match well with the cut-checked WPDs, which further confirms the capability of the developed network.

Figure 17:
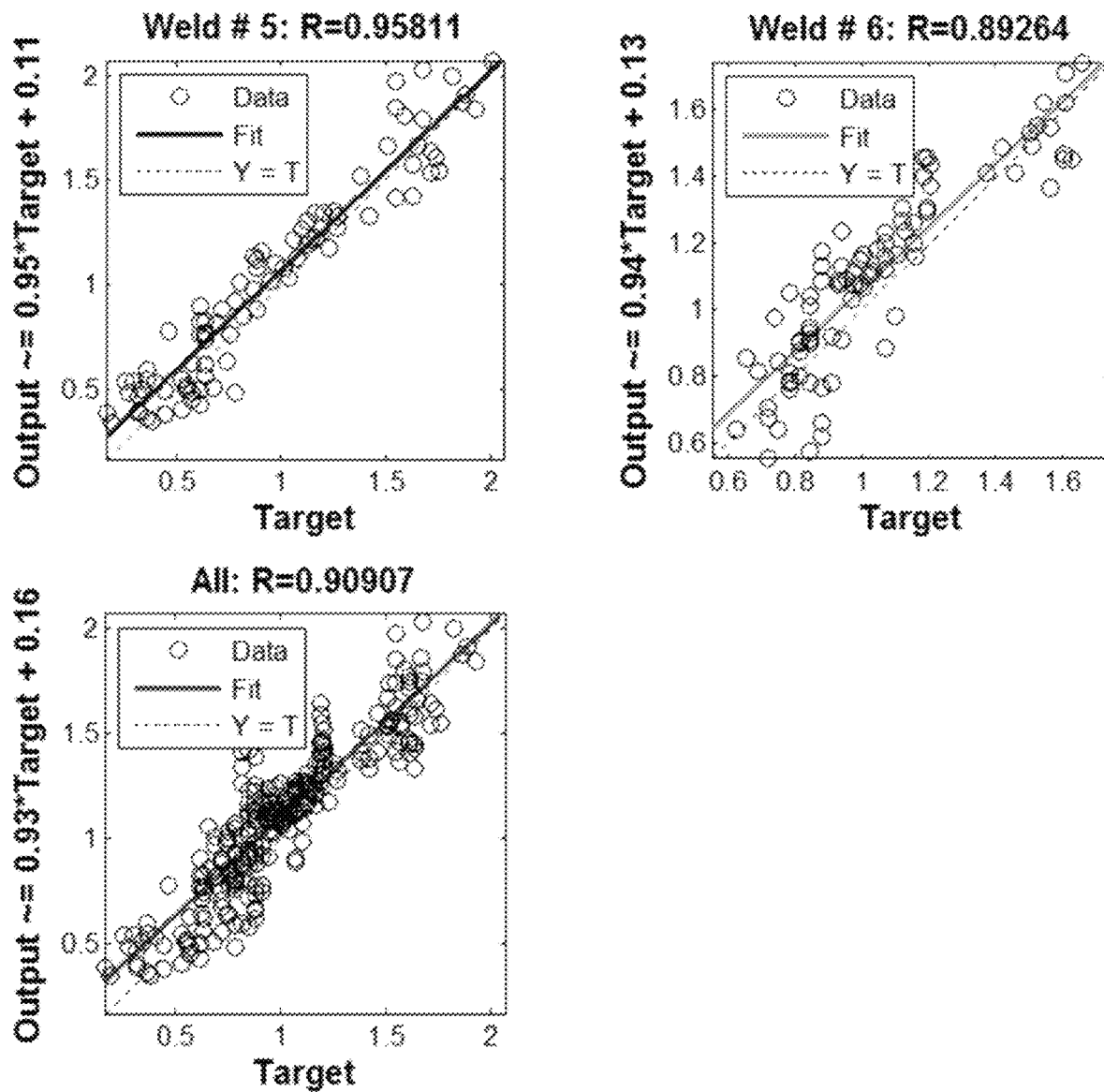
FIG. 17 shows regression plots of network outputs and targets for welds 5-6.

FIG. 17 shows the regression plots of network outputs and targets for the additional test data. Weld 5 has an R value of 0.95811. Weld 6 has an R value of 0.89264, which is lower than weld 5 partially because the range of WPDs in weld 6 is small. The combined R value for the two welds is 0.90907, which is acceptable.

Regression Analysis

For the purpose of comparison, regression models were developed to predict WPDs based on transmission coefficients of selected Lamb waves and the LEU signal energy. Since there was no guideline to determine the form of the regression model, linear regressions were used.

As seen in FIG. 10, transmission coefficients of some Lamb waves exhibit nonlinear relationships with WPDs. For these Lamb waves, square root and quadratic terms of their transmission coefficients were included to account for the nonlinearity. TABLE 3 lists the terms included in the full model.

| Lamb Mode | Frequency (MHz) | Linear Term | Square Root Term | Quad Term | Lamb Mode | Frequency (MHz) | Linear Term | Square Root Term | Quad Term |
|---|---|---|---|---|---|---|---|---|---|
| A0 | 0.4586 | ✓ | ✓ | ✓ | A1 | 0.9211 | ✓ | | |
| | 0.667 | ✓ | ✓ | ✓ | | 1.161 | ✓ | | |
| | 0.8362 | ✓ | | | S1 | 1.009 | ✓ | | |
| | 0.9776 | ✓ | | | | 1.013 | ✓ | | |
| | 1.144 | ✓ | | | | 1.022 | ✓ | | |
| | 1.411 | ✓ | | | S1 | 1.04 | ✓ | ✓ | ✓ |
| S0 | 0.6157 | ✓ | ✓ | ✓ | | 1.061 | ✓ | | |
| | 0.6474 | ✓ | ✓ | ✓ | | 1.078 | ✓ | | |
| | 0.6871 | ✓ | | | Energy | | ✓ | | |
| | 0.9713 | ✓ | | | | | | | |
| | 1.006 | ✓ | | | | | | | |
| | 1.05 | ✓ | | | | | | | |
| | 1.119 | ✓ | | | | | | | |
| | 1.154 | ✓ | | | | | | | |
| | 1.233 | ✓ | | | | | | | |

Scatter plots of some Lamb waves are similar, which means they are correlated. The developed neural network used all of them because the redundancy of information helped to improve its fault-tolerance capability. However, in regression analysis, fewer predictors are preferred.

The forward stepwise method was used to search for the best model based on the Akaike Information Criterion (AIC). The selected terms using the forward stepwise method are highlighted in TABLE 3. Welds 1-4 were used to develop the model.

Figure 18:
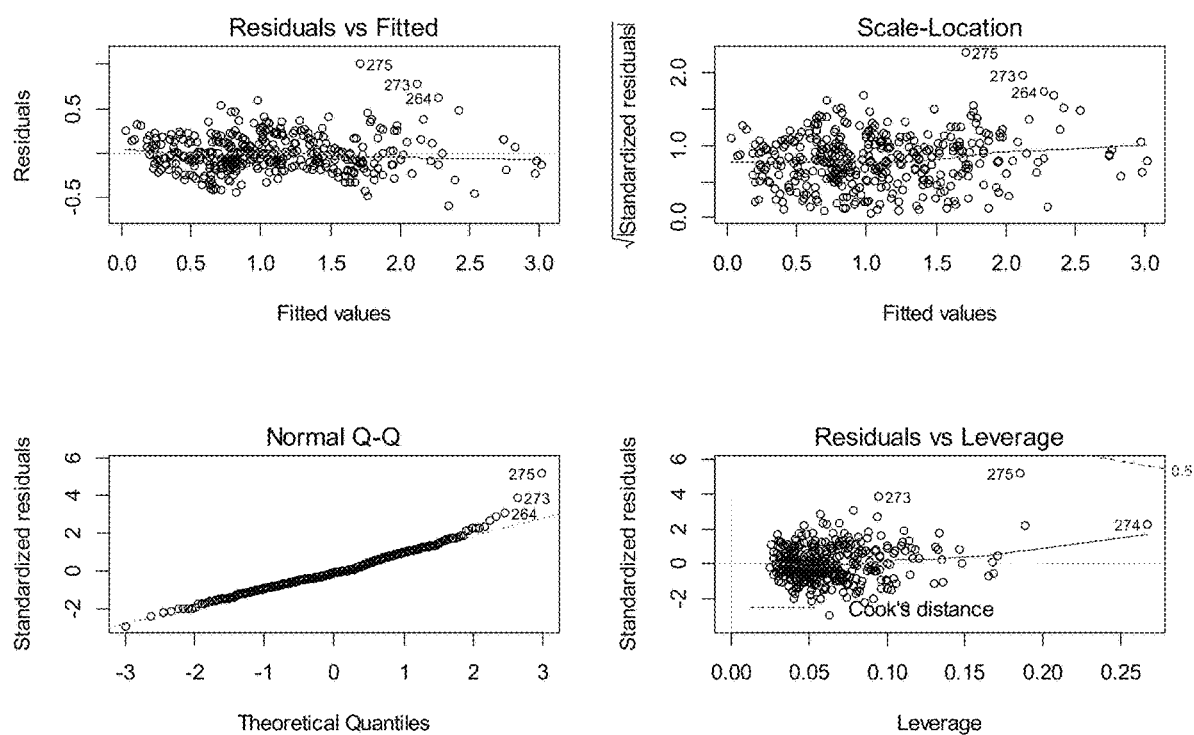
FIG. 18 shows diagnostic plots of selected model using model development data.

FIG. 18 shows the diagnostic plots of the selected model. There is no pattern in the residual plots, which means the selected model didn't miss any significant information. For the model development data, the predicted and the cut-checked WPDs have an R value of 0.9426.

Figure 19A:
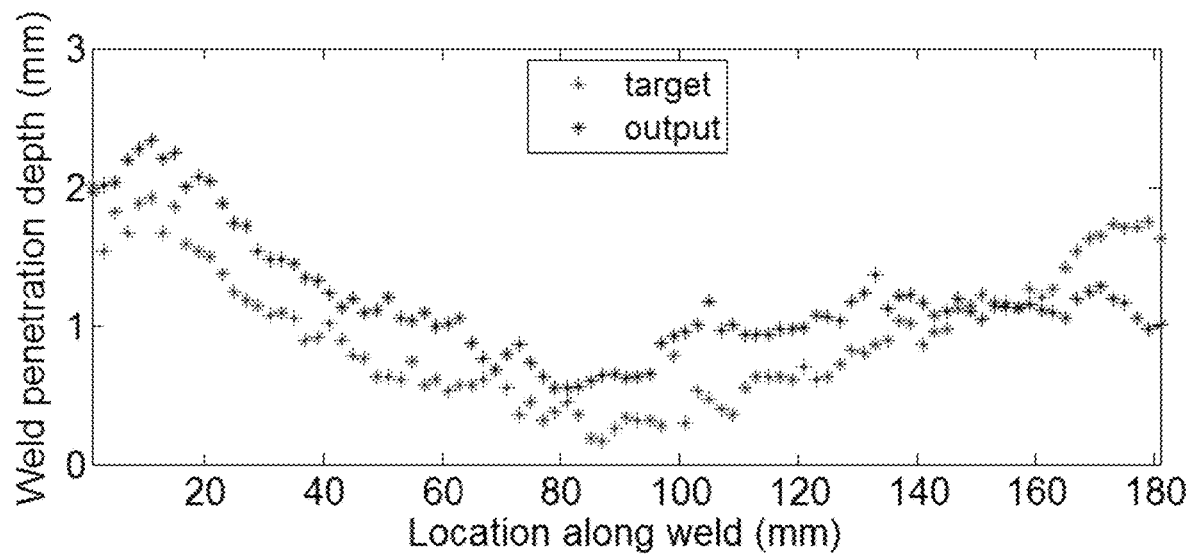
FIGS. 19(a)-(b) are a comparison of regression outputs and targets for (a) weld 5, and (b) weld 6.
Figure 19B:
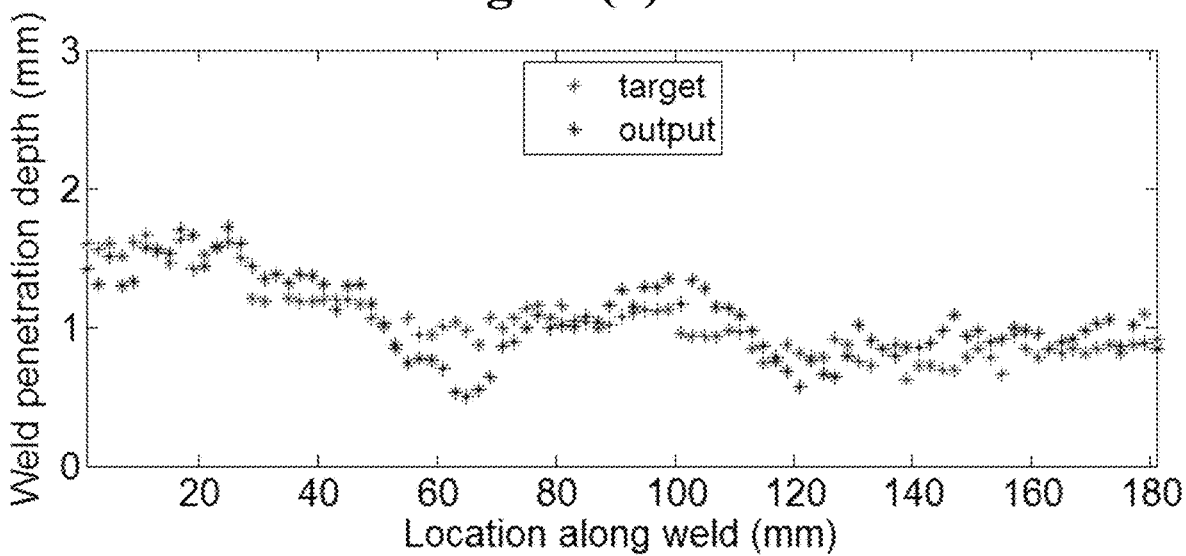

Welds 5-6 were used to validate the selected model. FIG. 19 shows the predicted WPDs and cut-checked WPDs along Welds 5-6.

Figure 20:
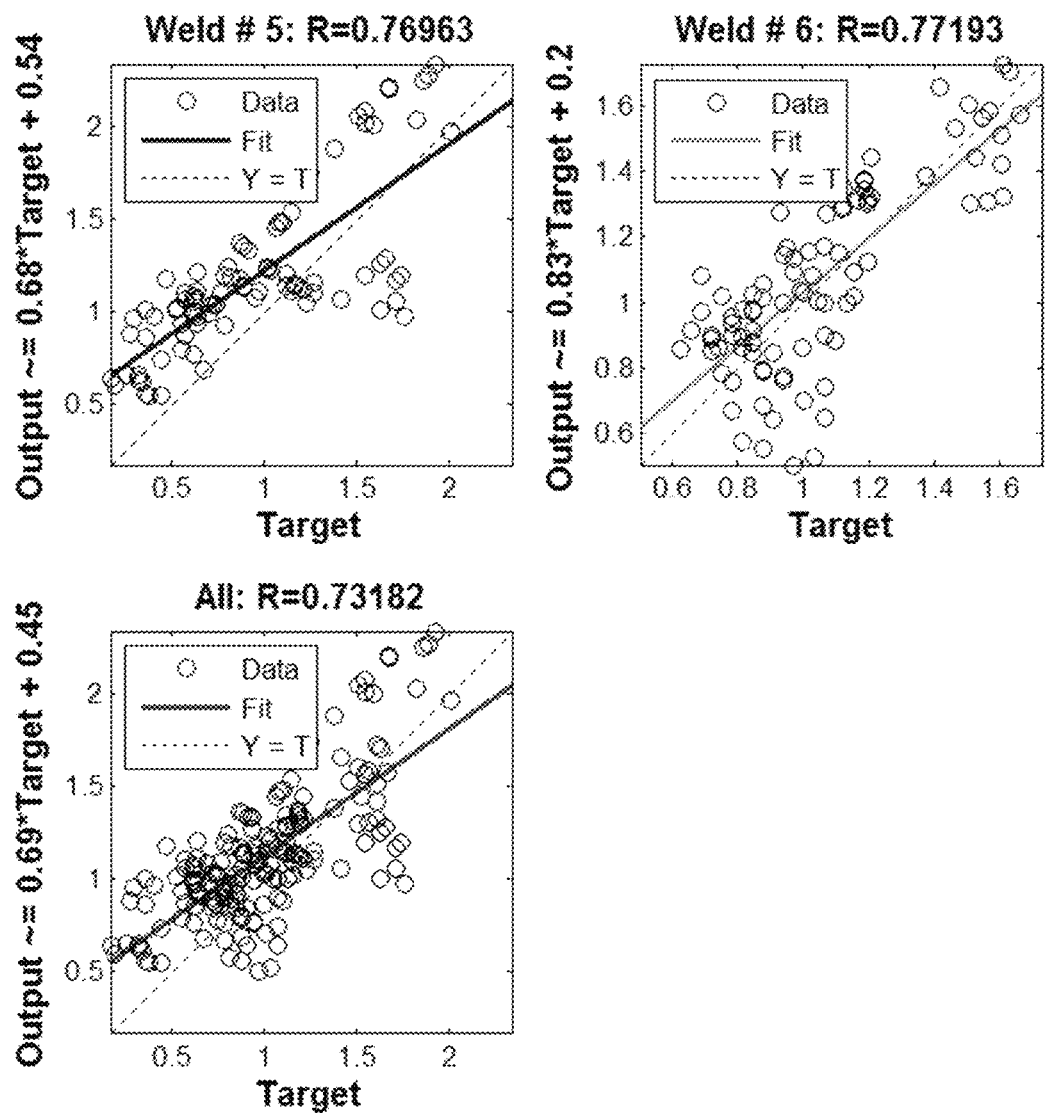
FIG. 20 shows regression plots of regression outputs and targets for validation data.

FIG. 20 shows the regression plots of regression predictions and targets for the two welds. For the validation data, the predicted and the cut-checked WPDs have a combined R value of 0.73182, which is much lower than the neural network predictions. This means that the underlying relationship was not fully captured by the selected regression model.

Localizations of Laser and EMAT in Inspection

The developed neural network proved the capability to predict WPDs in thin structures accurately. The laser and the EMAT need to be positioned properly in order to obtain high-quality signals.

Figure 21:
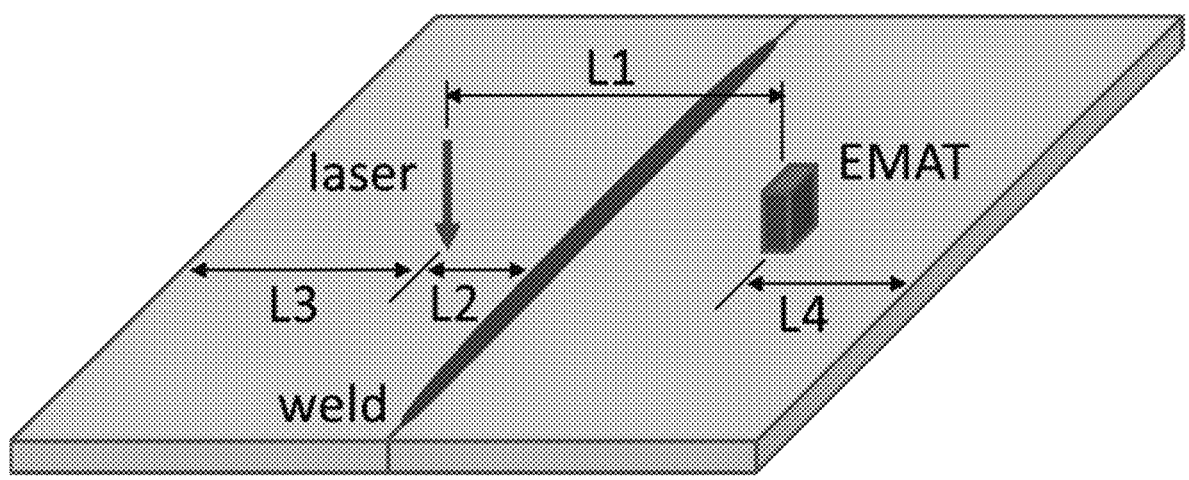
FIG. 21 is a diagram showing important distances of LEU technique.

FIG. 21 shows four important distances in inspection. L1 is the distance from the laser to the EMAT. L2 is the distance from the laser to the weld. L3 is the distance from the laser to the laser-side edge, and L4 is the distance from the EMAT to the EMAT-side edge.

Distance from Laser to EMAT

Figure 22:
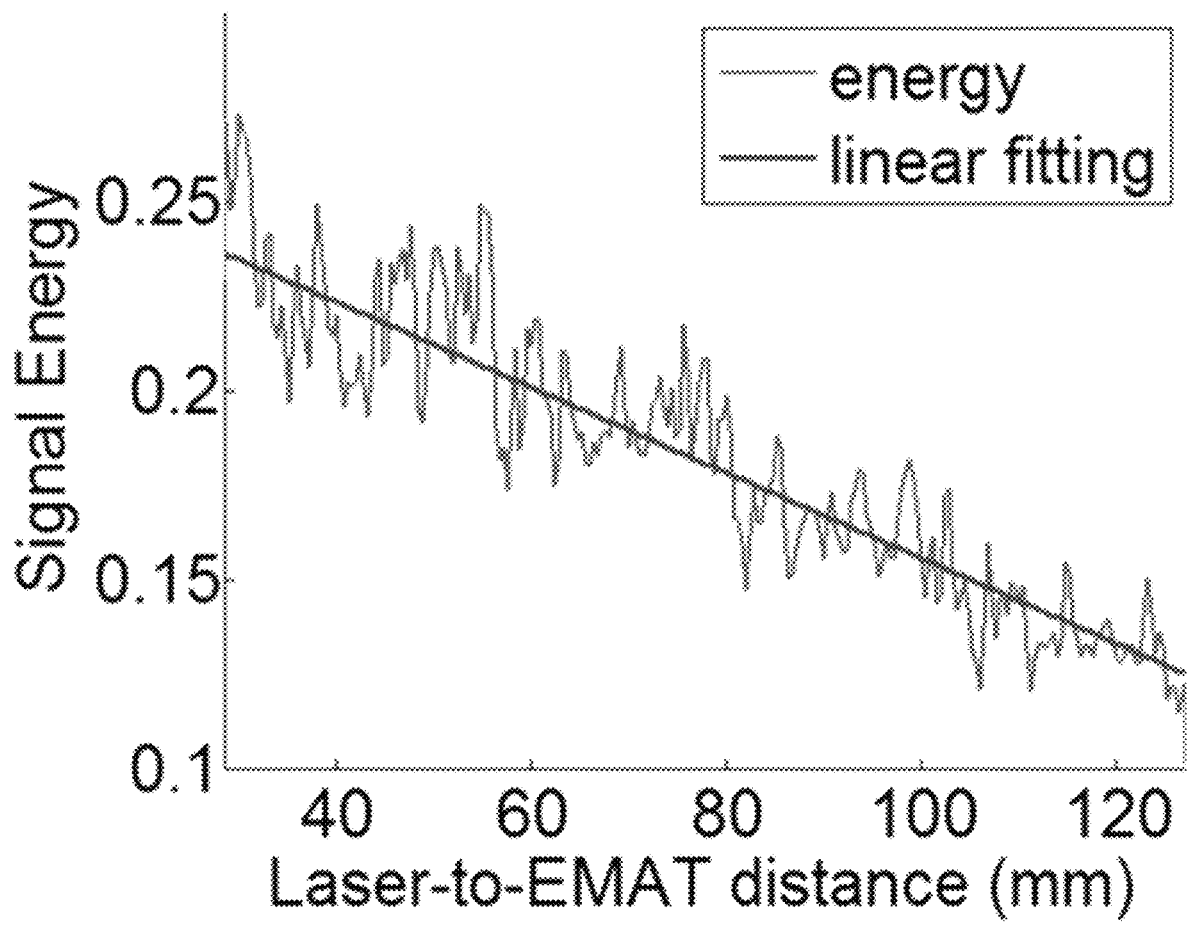
FIG. 22 is a graph of the LEU signal energy vs. laser-to-EMAT distance.

If the laser-to-EMAT distance is too large, the SNR of LEU signals will be low due to attenuations of laser-generated Lamb waves. FIG. 22 shows how fast the LEU signal energy decreases with increasing laser-to-EMAT distance. A linear fitting estimates that the LEU signal energy reduces at a rate of 0.4% per mm and that the LEU signal will die out after propagating for a maximum of 237 mm. Plus, a large laser-to-EMAT distance makes the LEU signals more vulnerable to reflections from sample edges, which will be explained in more details later.

Figure 23A:
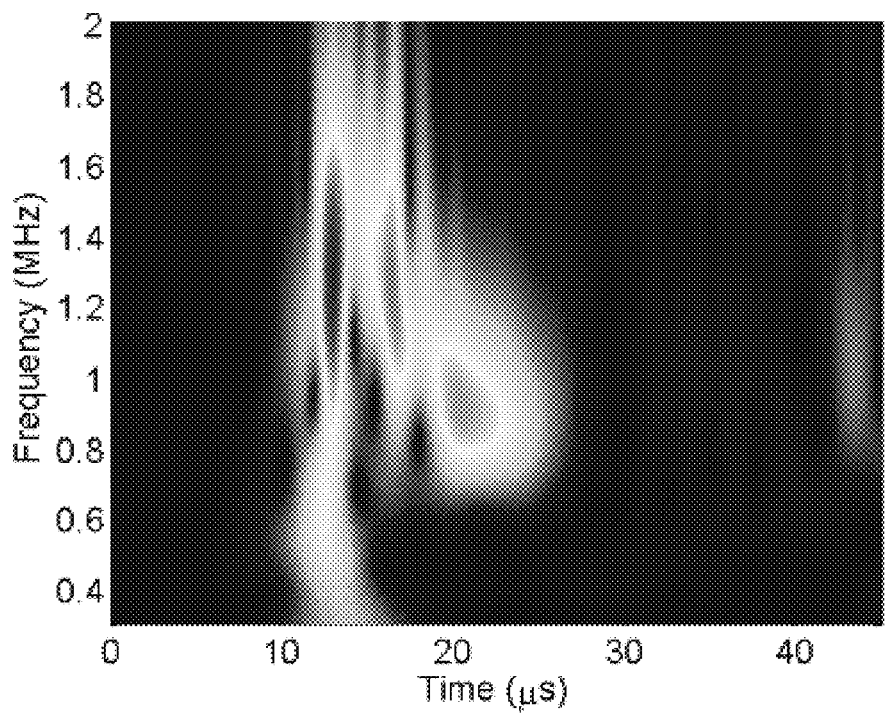
FIGS. 23(a)-(b) are CWT plots of signals acquired at different laser-to-EMAT distances; (a) Laser-to-EMAT distance=35 mm, and (b) Laser-to-EMAT distance=64 mm.
Figure 23B:
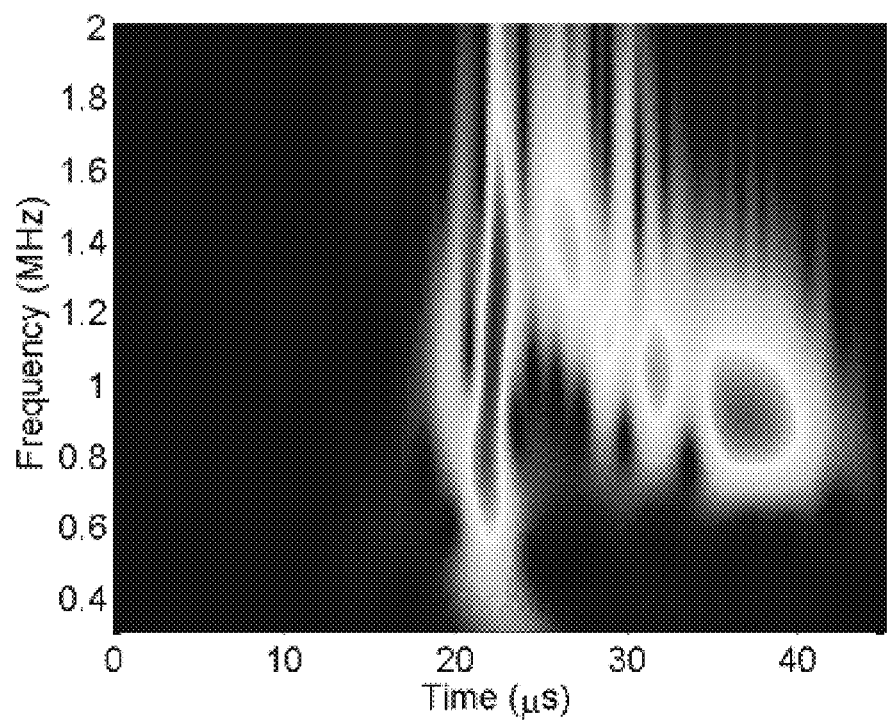
Figure 24:
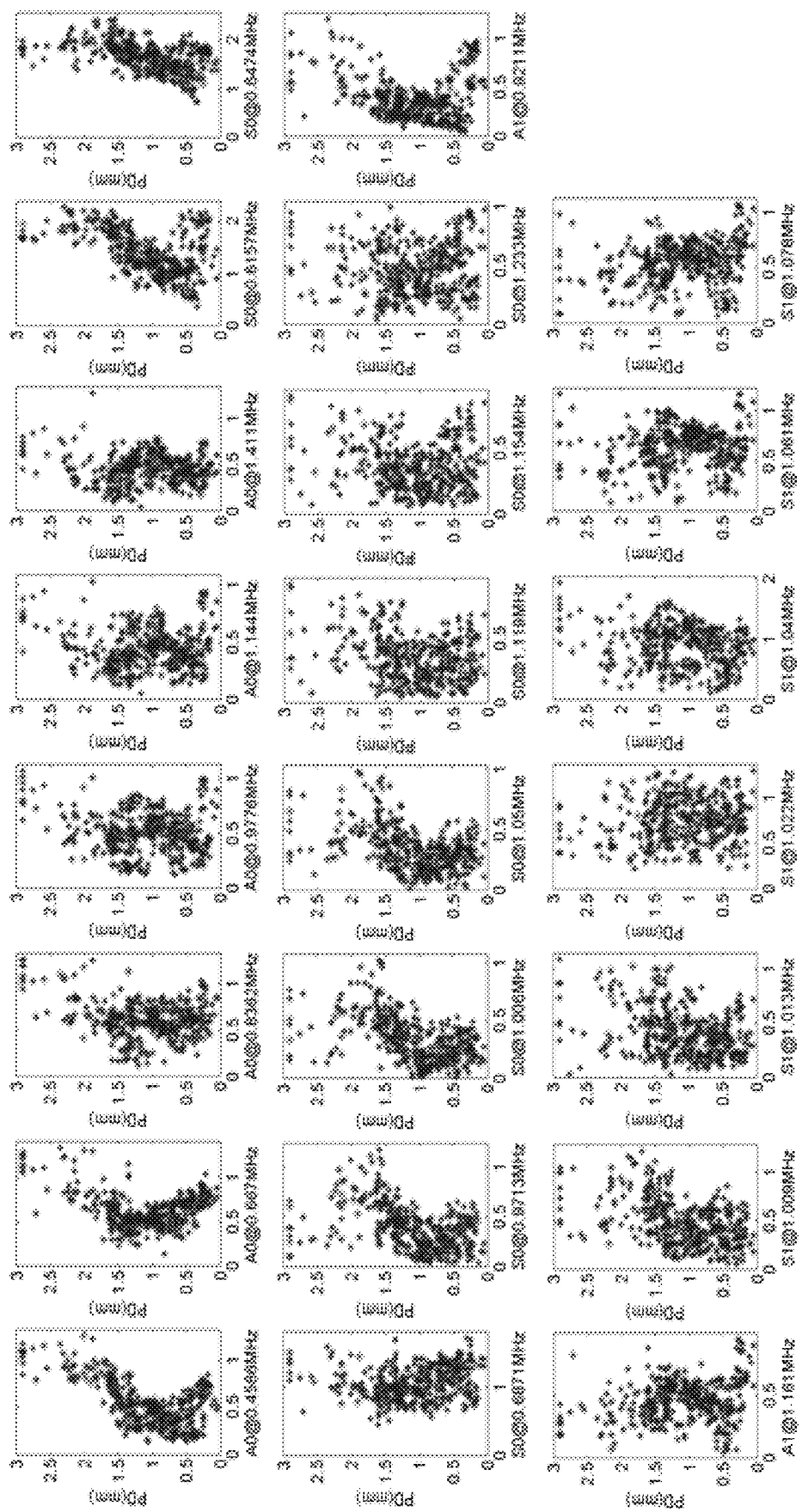
FIG. 24 shows scatter plots of selected Lamb waves when laser-to-weld distance is 7 mm.
Figure 25:
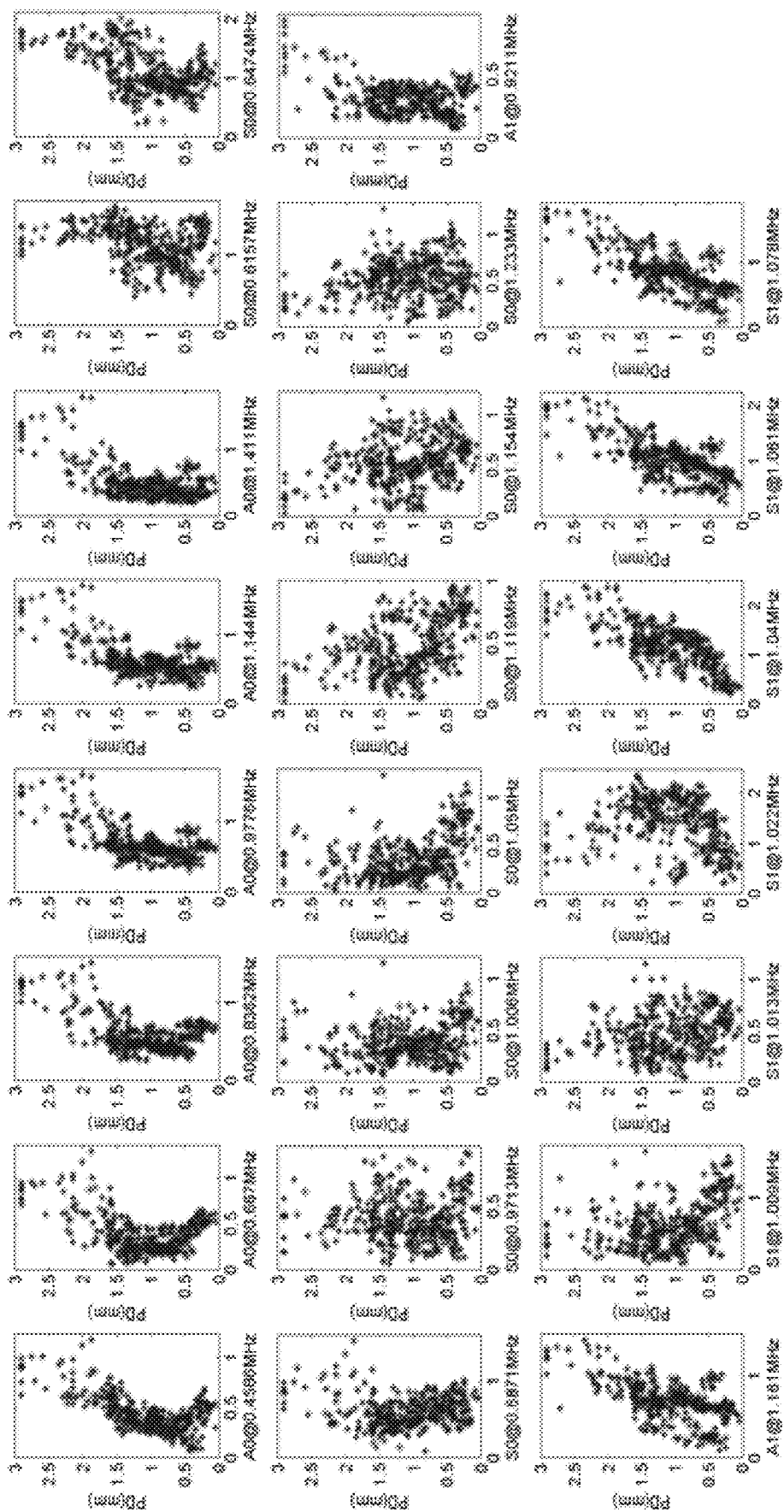
FIG. 25 shows scatter plots of selected Lamb waves when laser-to-weld distance is 17 mm.
Figure 26:
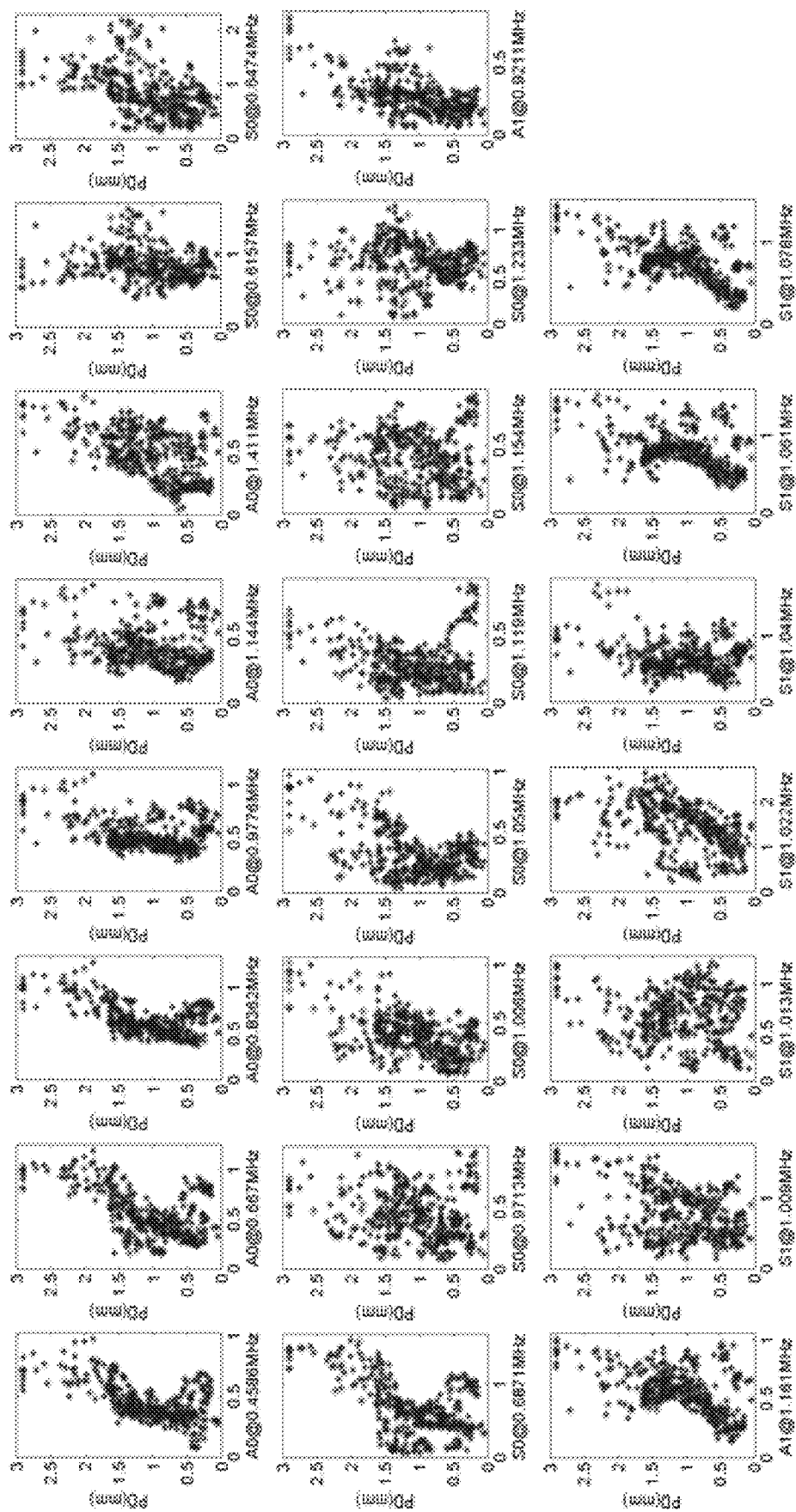
FIG. 26 shows scatter plots of selected Lamb waves when laser-to-weld distance is 27 mm.
Figure 27:
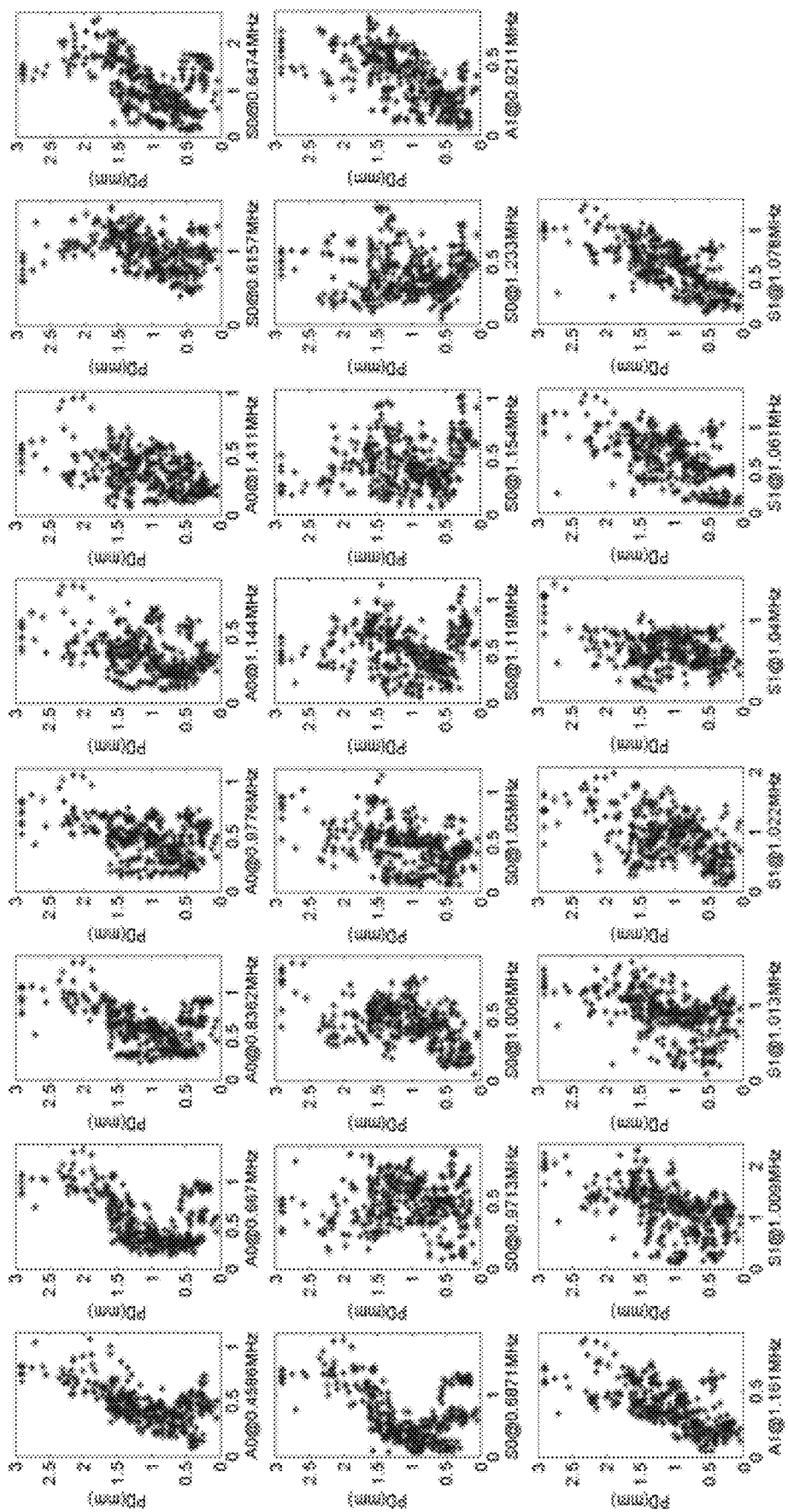
FIG. 27 shows scatter plots of selected Lamb waves when laser-to-weld distance is 37 mm.

FIGS. 23($a$)-($b$) show CWT plots of two signals acquired at different laser-to-EMAT distances. If the laser-to-EMAT distance is too small, different Lamb waves in LEU signals are not separated enough in the time-frequency domain, which will affect calculations of their transmission coefficients. Given the size of samples used in this work, the laser-to-EMAT distance was set to 64 mm, which proved to provide a good balance between the SNR and the capability to separate different Lamb waves.

Distance from Laser to Weld

During LEU inspection, the laser-to-weld distance was changed from 7 mm to 47 mm at increments of 10 mm to investigate its effect on the signal quality.

FIGS. 24-27 show the scatter plots of 23 selected Lamb waves when the laser-to-weld distance equals 7 mm, 17 mm, 27 mm, and 37 mm, respectively. Comparison with FIG. 10 shows that when the laser-to-weld distance equals 47 mm, the scatter plots of the selected Lamb waves have the clearest patterns. This means that LEU signals are more sensitive to varying WPDs when the EMAT is positioned close to weld seams. In this work, the ANN was trained with data acquired when the laser-to-weld distance was set to 47 mm. The EMAT-to-weld distance was 17 mm, accordingly.

Distance from Laser to Laser-side Edge

Figure 28A:
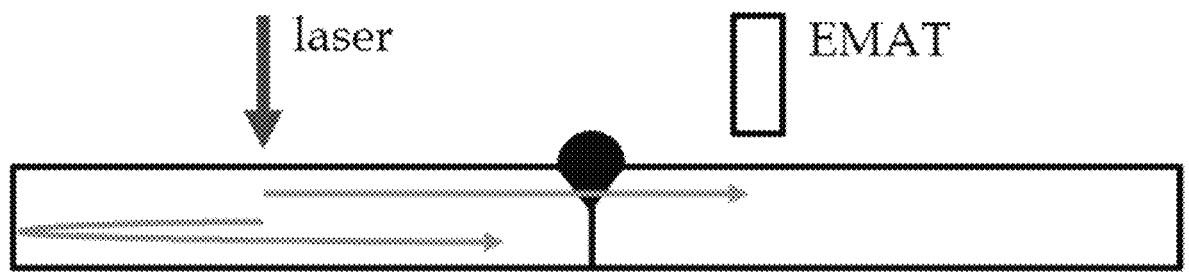
FIGS. 28(a)-(b) are diagrams showing edge reflections.
Figure 28B:
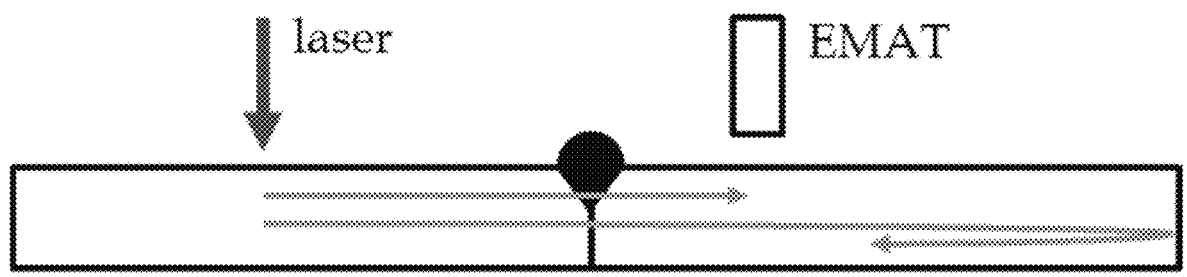

The laser should be positioned far enough from sample edges, otherwise reflections from the laser-side edge can contaminate the received LEU signals, as shown in FIG. 28($a$), and the calculated transmission coefficients will be affected. The fastest Lamb wave identified in LEU signals travels at a speed of 3697 m/s. The slowest Lamb wave whose transmission coefficient is selected to predict WPDs travels at a speed of 2004 m/s.

The laser-to-edge distance should be large enough so that the reflection of the fasted Lamb wave cannot catch up with the slowest Lamb wave before the slowest Lamb wave reaches the EMAT. The minimum value for the laser-to-edge distance can be calculated using Eq. 2, which is 27 mm when the laser-to-EMAT distance is 64 mm. Eq. 2 shows that increasing the laser-to-EMAT distance will increase the minimum acceptable value for the laser-to-edge distance.

$$D_{min} = \frac{C_{fastest} - C_{slowest}}{2C_{slowest}} D_{laser-EMAT} \quad (2)$$

Distance from EMAT to EMAT-side Edge

For the same reason, the EMAT receiver should be positioned far enough from the EMAT-side edge, as shown in FIG. 25(b). The minimum value for the EMAT-to-edge distance can be also determined using Eq. 2, which is 27 mm when the laser-to-EMAT distance is 64 mm. Increasing the laser-to-EMAT distance will also increase the minimum acceptable value for the EMAT-to-edge distance.

Effect of Residual Stresses on Predictions

Arc welding processes introduce residual stresses into welds due to uneven cooling speeds of molten metals. Typically after the welding process, heat treating is used to relieve the residual stresses, which is called stress relief. For A36 steel, the recommended temperature is from 1100°-1250° F. (593° C.-676° C.), and the recommended soak time is one hour per inch of thickness.

Figure 29:
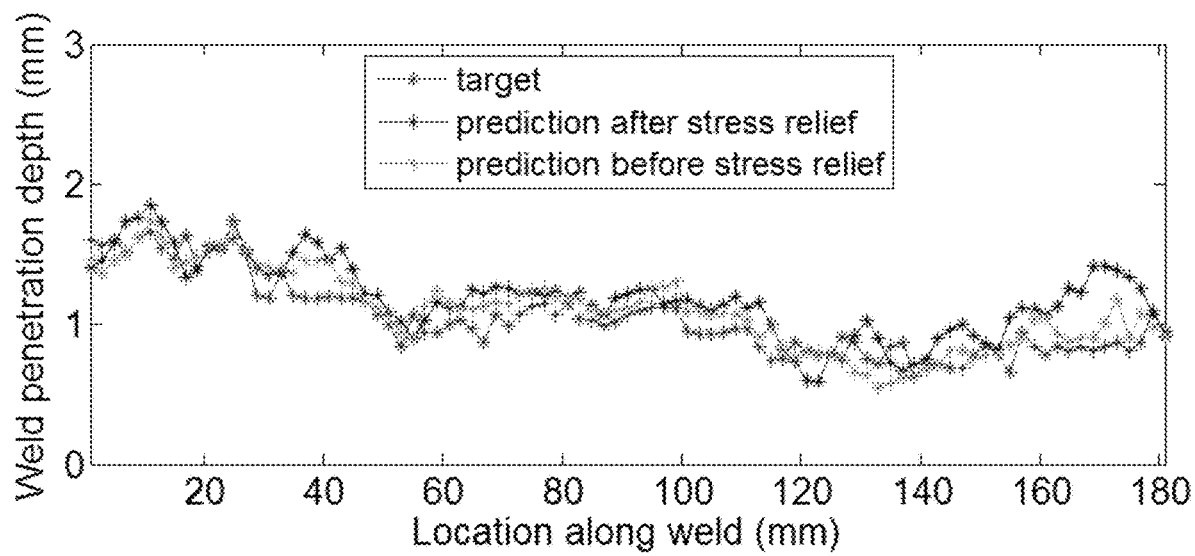
FIG. 29 is a graph of a comparison of predictions before and after stress relief for weld 6.
Figure 30:
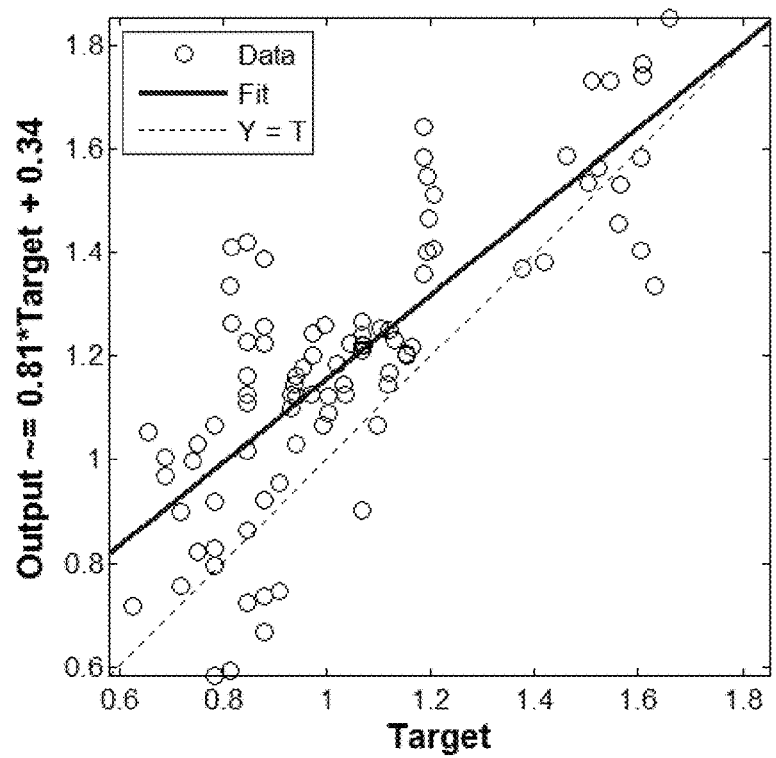
FIG. 30 is a regression plots of predictions and targets after weld 6 is stress relieved.

Weld 6 was stress relieved and inspected again before cut-check to study the effect of residual stresses on the network predictions. FIG. 29 shows the predicted WPDs before and after the stress relief process.

FIG. 29 shows the regression of the predicted and cut-checked WPDs after stress relief. The R value drops from 0.89264 to 0.78412, which indicates that the presence of residual stresses will affect the calculated transmissions of selected Lamb waves and lower the prediction accuracy. It is recommended that a different network be trained to predict WPDs which are stress relieved.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. An apparatus for non-destructively analyzing a weld in a sample comprising:
    an elastic wave source for generating elastic waves in the sample on one side of a weld seam;
    an elastic wave sensor disposed on an opposite side of the weld seam from the elastic wave source for detecting elastic waves that are propagated from the one side of the weld seam to the opposite side;
    an assembly for moving the elastic wave source and the elastic wave sensor along a portion of the length of the weld seam; and
    a processor assembly configured to process a transmission coefficient of the elastic wave sensed at a sensed location along the length of the weld seam to compute a weld penetration depth at the sensed location.

2. The apparatus of claim 1, wherein a plurality of weld penetration depths are computed at a plurality of sensed locations within the portion of the length of the weld seam traversed by the elastic wave source and the elastic wave sensor.

3. The apparatus of claim 2, wherein the processor assembly is further configured to convert the elastic wave sensed at the sensed location into its time-frequency domain.

4. The apparatus of claim 2, wherein the processor assembly is further configured to convert the elastic wave sensed at the sensed location into its time-frequency domain using complex-valued Morlet wavelets and continuous wavelet transform (CWT).

5. The apparatus of claim 4, wherein the processor assembly is further configured to calculate a transmission coefficient of the elastic wave at a sensed location based on the CWT of a signal received by the elastic wave sensor.

6. The apparatus of claim 5, wherein the processor assembly comprises a neural network developed from the transmission coefficients and the signal energy to compute the weld penetration depths at the sensed locations.

7. The apparatus of claim 1, wherein the elastic wave source comprises a pulsed Nd:YAG laser.

8. The apparatus of claim 1, wherein the elastic wave sensor comprises an electromagnetic acoustic transducer.

9. A method for measuring weld penetration depths using the apparatus of claim 1 comprising:
    exciting broadband Lamb waves in the sample from one side of the weld seam by the elastic wave source comprising an Nd:YAG pulsed laser;
    detecting the Lamb waves with the elastic wave sensor comprising a receiver on the other side of the weld seam;
    providing relative movement with the assembly between the laser and receiver and a portion of the length of the weld seam; and
    computing the weld penetration depth at the sensed location with the processor by:
        converting the Lamb wave signals received from the receiver to their time-frequency domains;
        calculating the transmission coefficients of different laser-generated Lamb waves based on the time-frequency domains of the signals; and
        developing a neural network with the transmission coefficients and the energies of the signals.

10. The method of claim 9, wherein providing relative movement comprises moving the sample along a portion of the length of the weld seam, past the laser and receiver.

11. The method of claim 10 further comprising delivering the laser through a convex lens to a focused point source on the sample.

12. The method of claim 9, wherein providing relative movement comprises moving the laser and receiver along a portion of the length of the weld seam.

13. A method for non-destructively analyzing a weld using the apparatus of claim 1 comprising:
    activating the elastic wave source comprising a pulsed, concentrated energy source to create the elastic waves comprising Lamb waves in the sample;
    receiving the Lamb waves with the elastic wave sensor comprising a receiver;
    storing signals generated by the receiver on a computer readable medium;
    providing relative movement with the assembly between the sample, the energy source and the receiver;

repeating the steps of activating, receiving, storing and providing relative movement until a predetermined analyzing length has been reached and the signals generated by the receiver have been stored on the computer readable medium;

creating a model correlating the signals generated by the receiver with empirical data for the sample;

retrieving the signals stored on the computer readable medium;

converting with the processor each signal to its time-frequency domain;

calculating with the processor the transmission coefficients of different laser-generated Lamb waves based on the time-frequency domain of the signal; and developing a neural network with the transmission coefficients and the signal energy;

wherein the neural network predicts the measuring weld penetration depths along the length of the weld.

14. The method of claim 13, wherein the energy source and the receiver do not exhibit relative movement between themselves.

15. The method of claim 14, wherein the energy source and the receiver move together along the analyzing length, and the sample remains fixed.

16. The method of claim 14, wherein the sample is moved along the analyzing length, and the energy source and the receiver remain fixed.

17. A system for non-destructively analyzing a weld seam in a sample comprising:
- a concentrated energy source for creating localized heating in the sample to cause Lamb waves;
- a receiver for receiving the Lamb waves;
- an assembly for providing relative movement of the sample, the energy source and the receiver along a portion of the length of the weld seam;
- a computer readable medium for storing one or more signals generated by the receiver; and
- a model for correlating the one or more signals generated by the receiver to empirical data.

18. The system of claim 17, where the energy source and the receiver do not exhibit relative movement as between themselves along a portion of the length of the weld seam.

* * * * *